US008673620B2

(12) United States Patent
Rivasseau et al.

(10) Patent No.: US 8,673,620 B2
(45) Date of Patent: Mar. 18, 2014

(54) **RADIORESISTANT ALGA OF THE *COCCOMYXA* GENUS**

(75) Inventors: Corinne Rivasseau, Cras (FR);
Emmanuel Farhi, Cras (FR); Alain Coute, Saint-Pierre du Perray (FR);
Ariane Atteia, Marseilles (FR)

(73) Assignees: Commissariat a l'Energie Atomique et aux Energies Alternatives, Paris (FR);
Institut Max Vcon Laue-Paul Langevin, Grenoble Cedex (FR); Centre Natioanl de al Recherche Scientifique, Paris (FR); Museum National d'Historie Naturelle, Paris (FR)

( * ) Notice: Subject to any disclaimer, the term of this patent is extended or adjusted under 35 U.S.C. 154(b) by 0 days.

(21) Appl. No.: 13/578,410

(22) PCT Filed: Feb. 11, 2011

(86) PCT No.: PCT/IB2011/050589
§ 371 (c)(1),
(2), (4) Date: Nov. 21, 2012

(87) PCT Pub. No.: WO2011/098979
PCT Pub. Date: Aug. 18, 2011

(65) Prior Publication Data
US 2013/0078707 A1    Mar. 28, 2013

(30) Foreign Application Priority Data

Feb. 12, 2010 (FR) .................................... 10 00578

(51) Int. Cl.
*C12N 1/12* (2006.01)
*C02F 3/34* (2006.01)

(52) U.S. Cl.
USPC ...................................... 435/257.1; 435/262.5

(58) Field of Classification Search
USPC ............................................ 435/257.1, 262.5
See application file for complete search history.

(56) References Cited

PUBLICATIONS

Rivasseau et al., An extremely radioresistant green eukaryote for radionuclide bio-decontamination in the nuclear industry, Energy Environ. Sci., 2013, 6, 1230.*
Farhi et al., Spectroscopic investigation of ionizing-radiation tolerance of a Chlorophyceae green micro-alga, Journal of Physics: Condensed Matter, vol. 20, pp. 1-7, 2008.
Rivasseau et al., Resistance to irradiation of micro-algae growing inthe storage pools of a nuclear reactor investigated by NMR and neutron spectroscopies, Spectroscopy, vol. 24, pp. 381-385, 2010.
Guschina et al., Lead and copper effects on lipid metabolism in cultured lichen photobionts with different phosphorus status, Phytochemistry, vol. 67, pp. 1731-1739, 2006.
Zoller et al., Slow algae, fast fungi: exceptionally high nucleotide substitution rate differences between lichenized fungi *Omphalina* and their symbiotic green algae *Coccomyxa*, Molecular Phylogenetics and Evolution, vol. 29, pp. 629-640, 2003.
International Search Report for PCT/IB2011/050589.

* cited by examiner

*Primary Examiner* — Karen Cochrane Carlson
*Assistant Examiner* — Jennifer M Tichy
(74) *Attorney, Agent, or Firm* — Morgan, Lewis & Bockius LLP

(57) ABSTRACT

The invention relates to novel algae of the *Coccomyxa* genus, in particular the algae of a novel species called *Coccomyxa actinabiotis*, and to the use thereof for metal uptake from aqueous media, and in particular from radioactive media.

10 Claims, 14 Drawing Sheets

A

B

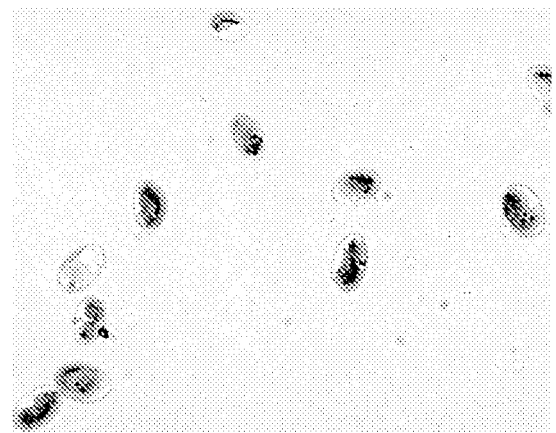
A
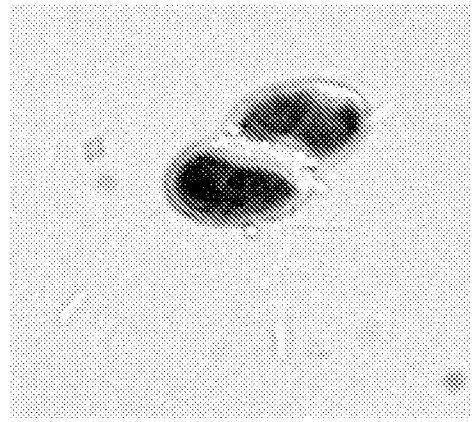
B
Figure 1

Figure 2

```
Coccomyxa_peltigerae      TCGACAATCTGGTTGATCCTGCCAGTAGTCATATGCTTGTCTCAAAGATT 50
Coccomyxa_chodatii        TCGACAATCTGGTTGATCCTGCCAGTAGTCATATGCTTGTCTCAAAGATT 50
C2003ILL6A                -CGACAATCTGGTTGATCCTGCCAGTAGTCATATGCTTGTCTCAAAGATT 49
Coccomyxa_sp_flensburg    ------ACCTGGTTGATCCTGCCAGTAGTCATATGCTTGTCTCAAAGATT 44
Coccomyxa_sp_CPCC         -----WACCTGGTTGATCCTGCCAGTAGTCATATGCTTGTCTCAAAGATT 45
Coccomyxa_glaronensis     -----AACCTGGTTGATCCTGCCAGTAGTCATATGCTTGTCTCAAAGATT 45
Chlamydomonas_sp          --------------------------------------------------

Coccomyxa_peltigerae      AAGCCATGCATGTCTAAGTATAAACTGCTTTATACTGTGAAACTGCGAGT 100
Coccomyxa_chodatii        AAGCCATGCATGTCTAAGTATAAACTGCTTTATACTGTGAAACTGCGAAT 100
C2003ILL6A                AAGCCATGCATGTCTAAGTATAAACTGCTTTATACTGTGAAACTGCGAAT 99
Coccomyxa_sp_flensburg    AAGCCATGCATGTCTAAGTATAAACTGATTTATACTGTGAAACTGCGAAT 94
Coccomyxa_sp_CPCC         AAGCCATGCATGTCTAAGTATAAACTGCTTTATACTGTGAAACTGCGAAT 95
Coccomyxa_glaronensis     AAGCCATGCATGTCTAAGTATAAACTGCTTTATACTGTGAAACTGCGAAT 95
Chlamydomonas_sp          --------------------------------------------------

Coccomyxa_peltigerae      GGCTCGTTAAATCAGTTATAGTTTATTTGATGGTACCTTACTACTCGGAT 150
Coccomyxa_chodatii        GGCTCATTAAATCAGTTATAGTTTATTTGATGGTACCTTACTACTCGGAT 150
C2003ILL6A                GGCTCATTAAATCAGTTATAGTTTATTTGATGGTACCTTGCTACTCGGAT 149
Coccomyxa_sp_flensburg    GGCTCATTAAATCAGTTATAGTTTATTTGATGGTACCTTGCTACTCGGAT 144
Coccomyxa_sp_CPCC         GGCTCATTAAATCAGTTATAGTTTATTTGATGGTACCTTGCTACTCGGAT 145
Coccomyxa_glaronensis     GGCTCATTAAATCAGTTATAGTTTATTTGATGGTACCTTGCTACTCGGAT 145
Chlamydomonas_sp          -GCTCATTAA-TCAGTTATAGTTTATTTGATGGTACCTT--TACTCGGAT 46
                           **** **** ******************************  *********

Coccomyxa_peltigerae      AACCGTAGTAATTCTAGAGCTAATACGTGCGGAAATCCCGACTTCCGGAA 200
Coccomyxa_chodatii        AACCGTAGTAATTCTAGAGCTAATACGTGCGAAATCCCGACTTCTGGAA 200
C2003ILL6A                AACCGTAGTAATTCTAGAGCTAATACGTGCGTAAATCCCGACTTCTGGAA 199
Coccomyxa_sp_flensburg    AACCGTAGTAATTCTAGAGCTAATACGTGCGGAAATCCCGACTTCCTGGAA 194
Coccomyxa_sp_CPCC         AACCGTAGTAATTCTAGAGCTAATACGTGCGGAAATCCCGACTTCTGGAA 195
Coccomyxa_glaronensis     AACCGTAGTAATTCTAGAGCTAATACGTGCGGAAATCCCGACTTCTGGAA 195
Chlamydomonas_sp          AACCGTAGTAATTCTAGAGCTAATACGTGCGTAAATCCCGACTTCTGGAA 96
                          ***********************************  ********** * ****

Coccomyxa_peltigerae      GGGACGTATTTATTAGATAAAAGGCCGACCCGGGCT-TGCCCGAAACGCGG 249
Coccomyxa_chodatii        GGGACGTATTTATTAGATAAAAGGCCGACCCGGGCT-TGCCCGAAACGCGG 249
C2003ILL6A                GGGACGTATTTATTAGATAAAAGGCCGACCCGACTCTGTCCGACTCGCGG 249
Coccomyxa_sp_flensburg    GGGACGTATTTATTAGATAAAAGGCCGACCCGACTCCGTCCGACTCGCGG 244
Coccomyxa_sp_CPCC         GGGACGTATTTATTAGATAAAAGGCCGACCCGACTCTGTCCGACTCGCGG 245
Coccomyxa_glaronensis     GGGACGTATTTATTAGATAAAAGGCCGACCCGACTC-GTCCGACTCGCGG 244
Chlamydomonas_sp          GGGACGTATTTATTAGATAAAAGGCCAGCCCGGGCT-TGCCCGACCTTAGG 145
                          ************************* **** ** * **** ** **

Coccomyxa_peltigerae      TGAATCATGATAACTCCACGAATCGCATGGCCTCAGTGCCGGCGATGTTT 299
Coccomyxa_chodatii        TGAATCATGATAACTCCACGAATCGCATGGCCTCAGTGCCGGCGATGTTT 299
C2003ILL6A                TGAATCATGATAACTCCACGAATCGCATGGCCTC-GAGCCGGCGATGTTT 298
Coccomyxa_sp_flensburg    TGAATCATGATAACTCCACGAATCGCATGGCC-CAGCGCCGGCGATGTTT 293
Coccomyxa_sp_CPCC         TCAATCATGATAACTCCACGAATCGCATGCCC-CACCGCCGGCGATGTTT 294
Coccomyxa_glaronensis     TGAATCATGATAACTCCACGAATCGCATGGCC-CAGCGCCGGCGATGTTT 293
Chlamydomonas_sp          CGAATCATGATAACTTCACGAATCGCATGGCC-TTGTGCCGGCGATGTTT 194
                           ************* **** **********   * ************

Coccomyxa_peltigerae      CATTCAAATTTCTGCCCTATCAACTTTCGACGGTAAGGTATTGGCTTACC 349
Coccomyxa_chodatii        CATTCAAATTTCTGCCCTATCAACTTTCGACGGTAAGGTATTGGCTTACC 349
C2003ILL6A                CATTCAAATTTCTGCCCTATCAACTTTCGACGGTAAGGTATTGGCTTACC 348
Coccomyxa_sp_flensburg    CATTCAAATTTCTGCCCTATCAACTTTCGACGGTAAGGTATTGGCTTACC 343
Coccomyxa_sp_CPCC         CATTCAAATTTCTGCCCTATCAACTTTCGACGGTAAGGTATTGGCTTACC 344
Coccomyxa_glaronensis     CATTCAAATTTCTGCCCTATCAACTTTCGACGGTAAGGTATTGGCTTACC 343
Chlamydomonas_sp          CATTCAAATTTCTGCCCTATCAACTTTCGATGGTAGGATAGAGGCCTACC 244
                          ***************************** **** * **  *** ****
```

Figure 3

```
Coccomyxa_peltigerae      GTGGTGGTAACGGGTGACGGAGGATTGGGGTTCGATTCCGGAGAGGGAGC 399
Coccomyxa_chodatii        GTGGTGGTAACGGGTGACGGAGGATTAGGGTTCGATTCCGGAGAGGGAGC 399
C2003ILL6A                GTGGTGGTAACGGGTGACGGAGGATTAGGGTTCGATTCCGGAGAGGGAGC 398
Coccomyxa_sp_flensburg    GTGGTGGTAACGGGTGACGGAGGATTAGGGTTCGATTCCGGAGAGGGAGC 393
Coccomyxa_sp_CPCC         GTGGTGGTAACGGGTGACGGAGGATTAGGGTTCGATTCCGGAGAGGGAGC 394
Coccomyxa_glaronensis     GTGGTGGTAACGGGTGACGGAGGATTAGGGTTCGATTCCGGAGAGGGAGC 393
Chlamydomonas_sp          ATGGTGGTAACGGGTGACGGAGGATTAGGGTTCGATTCCGGAGAGGGAGC 294
                           *************************  ***********************

Coccomyxa_peltigerae      CTGAGAAACGGCAACCACATCCAAGGAAGGCAGCAGGCGCGCAAATTACC 449
Coccomyxa_chodatii        CAGAGAAACGGCTACCACATCCAAGGAAGGCAGCAGGCGCGCAAATTACC 449
C2003ILL6A                CTGAGAAACGGCTACCACATCCAAGGAAGGCAGCAGGCGCGCAAATTACC 448
Coccomyxa_sp_flensburg    CTGAGAAACGGCTACCACATCCAAGGAAGGCAGCAGGCGCGCAAATTACC 443
Coccomyxa_sp_CPCC         CTGAGAAACGGCTACCACATCCAAGGAAGGCAGCAGGCGCGCAAATTACC 444
Coccomyxa_glaronensis     CTGAGAAACGGCTACCACATCCAAGGAAGGCAGCAGGCGCGCAAATTACC 443
Chlamydomonas_sp          CTGAGAAACGGCTACCACATCCAAGGAAGGCAGCAGGCGCGCAAATTACC 344
                          * ********* **************************************

Coccomyxa_peltigerae      CAATCTTGACACAAGGAGGTAGTGACAATGAATAACAATACCGGGGTTTT 499
Coccomyxa_chodatii        CAATCTTGACACAAGGAGGTAGTGACAATAAATAACAATACCGGGGTTTT 499
C2003ILL6A                CAATCTTGACACAAGGAGGTAGTGACAATAAATAACAATACCGGGGTTTT 498
Coccomyxa_sp_flensburg    CAATCTTGACACAAGGAGGTAGTGACAATAAATAACAATACCGGGGTTAT 493
Coccomyxa_sp_CPCC         CAATCTTGACACAAGGAGGTAGTGACAATAAATAACAATACCGGGGTTAT 494
Coccomyxa_glaronensis     CAATCTTGACACAAGGAGGTAGTGACAATAAATAACAATACCGGGGTTTT 493
Chlamydomonas_sp          CAATCCCGACACGGGGAGGTAGTGACAATAAATAACAATACCGGGCATCT 394
                          *****  *****  ********************  *********  * *

Coccomyxa_peltigerae      TCAACTCTGGTAATTGGAATGAGTACAATCTAAACCCCTTAACGAGGATC 549
Coccomyxa_chodatii        TCAACTCTGGTAATTGGAATGAGTACAATCTAAACCCCTTAACGAGGATC 549
C2003ILL6A                TCAACTCTGGTAATTGGAATGAGTACAATCTAAACCCCTTAACGAGGATC 548
Coccomyxa_sp_flensburg    TCAACTCTGGTAATTGGAATGAGTACAATCTAAACCCCTTAATGAGGATC 543
Coccomyxa_sp_CPCC         TCAACTCTGGTAATTGGAATGAGTACAATCTAAACCCCTTAACGAGGATC 544
Coccomyxa_glaronensis     TCAACTCTGGTAATTGGAATGAGTACAATCTAAACCCCTTAACGAGGATC 543
Chlamydomonas_sp          TTG--TCTGGTAATTGGAATGAGTACAATGTAAATATCTTAACGAGTATC 442
                          *    ************************ ****    ***** *** ***

Coccomyxa_peltigerae      AATTGGAGGGCAAGTCTGGTGCCAGCAGCCGCGGTAATTCCAGCTCCAAT 599
Coccomyxa_chodatii        AATTGGAGGGCAAGTCTGGTGCCAGCAGCCGCGGTAATTCCAGCTCCAAT 599
C2003ILL6A                AATTGGAGGGCAAGTCTGGTGCCAGCAGCCGCGGTAATTCCAGCTCCAAT 598
Coccomyxa_sp_flensburg    AATTGGAGGGCAAGTCTGGTGCCAGCAGCCCCGGTAATTCCAGCTCCAAT 593
Coccomyxa_sp_CPCC         AATTGGAGGGCAAGTCTGGTGCCAGCAGCCGCGGTAATTCCAGCTCCAAT 594
Coccomyxa_glaronensis     AATTGGAGGGCAAGTCTGGTGCCAGCAGCCGCGGTAATTCCAGCTCCAAT 593
Chlamydomonas_sp          CATTGGAGGGCAAGTCTGGTGCCAGCAGCCGCGGTAATTCCAGCTCCAAT 492
                           ****************************** ******************

Coccomyxa_peltigerae      AGCGTATATTTAAGTTGTTGCAGTTAAAAAGCTCGTAGTTGGATTTCGGG 649
Coccomyxa_chodatii        AGCGTATATTTAAGTTGTTGCAGTTAAAAAGCTCGTAGTTGGATCTCGGG 649
C2003ILL6A                AGCGTATATTTAAGTTGTTGCAGTTAAAAAGCTCGTAGTTGGATTTCGGG 648
Coccomyxa_sp_flensburg    AGCGTATATTTAAGTTGTTGCAGTTAAAAAGCTCGTAGTTGGATTTCGGG 643
Coccomyxa_sp_CPCC         AGCGTATATTTAAGTTGTTGCAGTTAAAAAGCTCGTAGTTGGATTTCGGG 644
Coccomyxa_glaronensis     AGCGTATATTTAAGTTGTTGCAGTTAAAAAGCTCGTAGTTGGATTTCGGG 643
Chlamydomonas_sp          AGCGTATATTTAAGTTGTTGCAGTTAAAAAGCTCGTAGTTGGATTTCGGG 542
                          ******************************************** *****

Coccomyxa_peltigerae      CGGGCCCGGCCGGTCCGCCTTCGGGTGTGCACTGACCGGGCCCGTCATGT 699
Coccomyxa_chodatii        CGGGCCCGGCCGGTCCGCCTTCGGGTGTGCACTGACCGGGCCCGTCTTGT 699
C2003ILL6A                CGGGCTCGGCCGGTCCGCCGTTCGGGTGTGCACTGACCGAGCCCGTCTTGT 698
Coccomyxa_sp_flensburg    CGGGCCCGGCCGGTCCGCCTCACGGTGTGCACTGACCGGGCCCGTCCTGC 693
Coccomyxa_sp_CPCC         CGGGCCCGGCCGGTCCGCCCTCACGGTGTGCACTGACCGGGCCCGTCCTGC 694
Coccomyxa_glaronensis     CGGGCCCGGCCGGTCCGCCTCACGGTGTGCACTGACCGGGCCCGTCCTGC 693
Chlamydomonas_sp          TGGGTTGCAGTGGTCTGCCACT-GGTATGTACTGCTGCCGGCTCACCTTTC 591
                           ***   **** ***  ***   ***  ** ****   **  *   * *
```

Figure 3 (continued)

```
Coccomyxa_peltigerae    TGCCGGGGACGGGCTCCTGGGCTTCACTGTCCGGGACTCGGAGTCGGCGA 749
Coccomyxa_chodatii      TGCCGGGGACGGGCTCCTGGGCTTCACTGTCCGGGACTCGGAGTCGGCGA 749
C2003ILL6A              TGCCGGGGACGGGCTCCTGGGCTTAACTGTCCGGGACTCGGAGTCGGCGA 748
Coccomyxa_sp_flensburg  TGCCGGGGACGGGCTCCTGGGCTTCACTGTCCGGGACTCGGAGTCGGCGA 743
Coccomyxa_sp_CPCC       TGCCGGGGACGGGCTCCTGGGCTTCACTGTCCGGGACTCGGAGTCGGCGA 744
Coccomyxa_glaronensis   TGCCGGGGACGGGCTCCTGGGCTTCACTGTCCGGGACTCGGAGTCGGCGA 743
Chlamydomonas_sp        TGCTGGGGACGGGCTCCTGGGCTTAACTGTCTGGGACTCGGAATCAGCGA 641
                        *** ****************** ****** ********** ** ****

Coccomyxa_peltigerae    GGTTACTTTGAGTAAATTAGAGTGTTCAAAGCAGGCCTACGCTCTGAATA 799
Coccomyxa_chodatii      GGTTACTTTGAGTAAATTAGAGTGTTCAAAGCAGGCCTACGCTCTGAATA 799
C2003ILL6A              GGTTACTTTGAGTAAATTAGAGTGTTCAAAGCAGGCCTACGCTCTGAATA 798
Coccomyxa_sp_flensburg  GGTTACTTTGAGTAAATTAGAGTGTTCAAAGCAGGCATCCGCCTTGAATA 793
Coccomyxa_sp_CPCC       GGTTACTTTGAGTAAATTAGAGTGTTCAAAGCAGGCATCCGCCTTGAATA 794
Coccomyxa_glaronensis   GGTTACTTTGAGTAAATTAGAGTGTTCAAAGCAGGCATCCGCCTTGAATA 793
Chlamydomonas_sp        AGTGACCTTGAGCAAAGTGAGTGTTCAAAGCAAGCCTACGCTCTGAAAC 691
                        ** ** ***** ***    ************* **  ***  ****

Coccomyxa_peltigerae    CATTAGCATGGAATAACACGA-TAGGACTCTGGCCTATCTTGTTGGTCTG 848
Coccomyxa_chodatii      CATTAGCATGGAATAACACGA-TAGGACTCTGGCCTATCTTGTTGGTCTG 848
C2003ILL6A              CATTAGCATGGAATAACACGAATAGGACTCTGGCCTATCTTGTTGGTCTG 848
Coccomyxa_sp_flensburg  CGTTAGCATGGAATAACACGA-TAGGACTCTGGCCTATCTTGTTGGTCTG 842
Coccomyxa_sp_CPCC       CGTTAGCATGCAATAACACCA-TACGACTCTGGCCTATCTTGTTGGTCTG 843
Coccomyxa_glaronensis   CGTTAGCATGGAATAACACGA-TAGGACTCTGGCCTATCTTGTTGGTCTG 842
Chlamydomonas_sp        ATTTAGCATGGGATCACACGA-TAGGACTCTGGCCTATCTTGTTGGTCTG 740
                        * ********* ** ****** ****************************

Coccomyxa_peltigerae    TGGGACCGGAGTAATGATTAAGAGGGACAGTCGGGGGCATTCGTATTTCA 898
Coccomyxa_chodatii      TGGGACCGGAGTGATGATTAAGAGGGACAGTCGGGGGCATTCGTATTTCA 898
C2003ILL6A              TGGGACCGGAGTAATGATTAAGAGGGACAGTCGGGGGCATTCGTATTTCA 898
Coccomyxa_sp_flensburg  TGGGACCGGAGTAATGATTAAGAGGGACAGTCGGGGGCATTCGTATTTCA 892
Coccomyxa_sp_CPCC       TGGGACCGGAGTAATGATTAAGAGGGACAGTCGGGGGCATTCGTATTTCA 893
Coccomyxa_glaronensis   TGGGACCGGAGTAATGATTAAGAGGGACAGTCGGGGGCATTCGTATTTCA 892
Chlamydomonas_sp        TAGGACCGGAGTAATGATTAAGAGGGACAGTCGGGGGCATTCGTATTTCA 790
                        * ********* **************************************

Coccomyxa_peltigerae    TTGTCAGAGGTGAAATTCTTGGATTTATGAAAGACGAACTACTGCGAAAG 948
Coccomyxa_chodatii      TTGTCAGAGGTGAAATTCTTGGATTTATGAAAGACGAACTACTGCGAAAG 948
C2003ILL6A              TTGTCAGAGGTGAAATTCTTGGATTTATGAAAGACGAACTACTGCGAAAG 948
Coccomyxa_sp_flensburg  TTGTCAGAGGTGAAATTCTTGGATTTATGAAAGACGAACTACTGCGAAAG 942
Coccomyxa_sp_CPCC       TTGTCAGAGGTGAAATTCTTGGATTTATGAAAGACGAACTACTGCGAAAG 943
Coccomyxa_glaronensis   TTGTCAGAGGTGAAATTCTTGGATTTATGAAAGACGAACTACTGCGAAAG 942
Chlamydomonas_sp        TTGTCAGAGGTGAAATTCTTGGATTTATGAAAGACGAACATCTGCGAAAG 840
                        **************************************  *********

Coccomyxa_peltigerae    CATTTGCCAAGGATGTTTTCATTAATCAAGAACGAAAGTTGGGGGCTCGA 998
Coccomyxa_chodatii      CATTTGCCAAGGATGTTTTCATTAATCAAGAACGAAAGTTGGGGGCTCGA 998
C2003ILL6A              CATTTGCCAAGGATGTTTTCATTAATCAAGAACGAAAGTTGGGGGCTCGA 998
Coccomyxa_sp_flensburg  CATTTGCCAAGGATGTTTTCATTAATCAAGAACGAAAGTTGGGGGCTCGA 992
Coccomyxa_sp_CPCC       CATTTGCCAAGGATGTTTTCATTAATCAAGAACGAAAGTTGGGGGCTCGA 993
Coccomyxa_glaronensis   CATTTGCCAAGGATGTTTTCATTAATCAAGAACGAAAGTTGGGGGCTCGA 992
Chlamydomonas_sp        CATTTGCCAAGGATGTTTTCATTGATCAAGAACGAAAGTTGGGGGCTCGA 890
                        *********************** **************************

Coccomyxa_peltigerae    AGACGATTAGATACCGTCCTAGTCTCAACCATAAACGATGCCGACTAGGG 1048
Coccomyxa_chodatii      AGACGATTAGATACCGTCCTAGTCTCAACCATAAACGATGCCGACTAGGG 1048
C2003ILL6A              AGACGATTAGATACCGTCCTAGTCTCAACCATAAACGATGCCGACTAGGG 1048
Coccomyxa_sp_flensburg  AGACGATTAGATACCGTCCTAGTCTCAACCATAAACGATGCCGACTAGGG 1042
Coccomyxa_sp_CPCC       AGACGATTAGATACCGTCCTAGTCTCAACCATAAACGATGCCGACTAGGG 1043
Coccomyxa_glaronensis   AGACGATTAGATACCGTCCTAGTCTCAACCATAAACGATGCCGACTAGGG 1042
Chlamydomonas_sp        AGACGATTAGATACCGTCGTAGTCTCAACCATAAACGATGCCGACTAGGG 940
                        ****************** *******************************
```

Figure 3 (continued)

```
Coccomyxa_peltigerae    ATTGGCGGGCGTTCTTTTGATGACCCCGCCAGCACCTTATGAGAAATCAA 1098
Coccomyxa_chodatii      ATTGGCGGGCGTTCTTTTGATGACCCCGCCAGCACCTTATGAGAAATCAA 1098
C2O03ILL6A              ATTGGCGGGCGTTCTTTTGATGACCTCGCCAGCACCTTATGAGAAATCAA 1098
Coccomyxa_sp_flensburg  ATTGGCGGGCGTTCTATTGATGACCCCGCCAGCACCTTATGAGAAATCAA 1092
Coccomyxa_sp_CPCC       ATTGGCGGGCGTTCTATTGATGACCCCGCCAGCACCTTATGAGAAATCAA 1093
Coccomyxa_glarcnensis   ATTGGCGGGCGTTCTATTGATGACCCCGCCAGCACCTTATGAGAAATCAA 1092
Chlamydomonas_sp        ATTGCCAGCTCTTTCGTTCATGACCCTGCCAGCACCTTATGACAAATCAA 990
                        ****** ** ***    ********   **********************

Coccomyxa_peltigerae    AGTTTTTGGGTTCCGGGGGGAGTATGGTCGCAAGGCTGAAACTTAAAGGA 1148
Coccomyxa_chodatii      AGTTTTTGGGTTCCGGGGGGAGTATGGTCGCAAGGCTGAAACTTAAAGGA 1148
C2O03ILL6A              AGTTTTTGGGTTCCGGGGGGAGTATGGTCGCAAGGCTGAAACTTAAAGGA 1148
Coccomyxa_sp_flensburg  AGTTTTTGGGTTCCGGGGGGAGTATGGTCGCAAGGCTGAAACTTAAAGGA 1142
Coccomyxa_sp_CPCC       AGTTTTTGGGTTCCGGGGGGAGTATGGTCGCAAGGCTGAAACTTAAAGGA 1143
Coccomyxa_glarcnensis   AGTTTTTGGGTTCCGGGGGGAGTATGGTCGCAAGGCTGAAACTTAAAGGA 1142
Chlamydomonas_sp        AGTTTTTGGGTTCCGGGGGGAGTATGGTCGCAAGGCTGAAACTTAAAGGA 1040
                        **************************************************

Coccomyxa_peltigerae    ATTGACGGAAGGGCACCACCAGGCGTGGA--------------------- 1177
Coccomyxa_chodatii      ATTGACGGAAGGGCACCACCAGGCGTGGA--------------------- 1177
C2O03ILL6A              ATTGACGGAAGGGCACCACCAGGCGTGGAATGTTCATGGCTTTGCGCCTC 1198
Coccomyxa_sp_flensburg  ATTGACGGAAGGGCACCACCAGGCGTGGA--------------------- 1171
Coccomyxa_sp_CPCC       ATTGACGGAAGGGCACCACCAGGCGTGGA--------------------- 1172
Coccomyxa_glarcnensis   ATTGACGGAAGGGCACCACCAGGCGTGGA--------------------- 1171
Chlamydomonas_sp        ATTGACGGAACGGCACCACCAGCCGTCGA--------------------- 1069
                        *****************************

Coccomyxa_peltigerae    --------------------------------------------------
Coccomyxa_chodatii      --------------------------------------------------
C2O03ILL6A              AGAGGGATGCTTTAACGAGTATCCCTAGTGCCTGGTTTCAGGACCAGGCG 1248
Coccomyxa_sp_flensburg  --------------------------------------------------
Coccomyxa_sp_CPCC       --------------------------------------------------
Coccomyxa_glarcnensis   --------------------------------------------------
Chlamydomonas_sp        --------------------------------------------------

Coccomyxa_peltigerae    --------------------------------------------------
Coccomyxa_chodatii      --------------------------------------------------
C2O03ILL6A              CAACACCGTCCAATTGCGGGGACTCCCTAAAGCTCGTGCACACCAAGCGG 1298
Coccomyxa_sp_flensburg  --------------------------------------------------
Coccomyxa_sp_CPCC       --------------------------------------------------
Coccomyxa_glarcnensis   --------------------------------------------------
Chlamydomonas_sp        --------------------------------------------------

Coccomyxa_peltigerae    --------------------------------------------------
Coccomyxa_chodatii      --------------------------------------------------
C2O03ILL6A              TGAGGGGAAACCCCATCGTGGCCAGGCCAATCACCTGGGTAAGGTAACAG 1348
Coccomyxa_sp_flensburg  --------------------------------------------------
Coccomyxa_sp_CPCC       --------------------------------------------------
Coccomyxa_glarcnensis   --------------------------------------------------
Chlamydomonas_sp        --------------------------------------------------

Coccomyxa_peltigerae    --------------------------------------------------
Coccomyxa_chodatii      --------------------------------------------------
C2O03ILL6A              TGGCGCGGCATGAAGGCGCAGTAATGTGCCTGAAATGGGTGATCCGCACC 1398
Coccomyxa_sp_flensburg  --------------------------------------------------
Coccomyxa_sp_CPCC       --------------------------------------------------
Coccomyxa_glarcnensis   --------------------------------------------------
Chlamydomonas_sp        --------------------------------------------------
```

Figure 3 (continued)

```
Coccomyxa_peltigerae    ----------------------------------------------------
Coccomyxa_chodatii      ----------------------------------------------------
C2003ILL6A              CAAGTCCTACAGAGCCCGGCCTGCCCGGGTTCCACGGATGCAGCTCACAG 1448
Coccomyxa_sp_flensburg  ----------------------------------------------------
Coccomyxa_sp_CPCC       ----------------------------------------------------
Coccomyxa_glaronensis   ----------------------------------------------------
Chlamydomonas_sp        ----------------------------------------------------

Coccomyxa_peltigerae    ----------------------------------------------------
Coccomyxa_chodatii      ----------------------------------------------------
C2003ILL6A              ACTAAATGGCGGTGGGTGTGATGCAATCATTTAGGAAACACACGTTCAGG 1498
Coccomyxa_sp_flensburg  ----------------------------------------------------
Coccomyxa_sp_CPCC       ----------------------------------------------------
Coccomyxa_glaronensis   ----------------------------------------------------
Chlamydomonas_sp        ----------------------------------------------------

Coccomyxa_peltigerae    ----------------------------------------------------
Coccomyxa_chodatii      ----------------------------------------------------
C2003ILL6A              AATTCAAGACAAAGAATTGTGGATTGTGAACATGTGAATTTGTCAAATAA 1548
Coccomyxa_sp_flensburg  ----------------------------------------------------
Coccomyxa_sp_CPCC       ----------------------------------------------------
Coccomyxa_glaronensis   ----------------------------------------------------
Chlamydomonas_sp        ----------------------------------------------------

Coccomyxa_peltigerae    ----------------------------------------------------
Coccomyxa_chodatii      ----------------------------------------------------
C2003ILL6A              ATGATTGTAACCATGCTTAAGATATAGTCGGACCACCTCGAAAGAGGCAC 1598
Coccomyxa_sp_flensburg  ----------------------------------------------------
Coccomyxa_sp_CPCC       ----------------------------------------------------
Coccomyxa_glaronensis   ----------------------------------------------------
Chlamydomonas_sp        ----------------------------------------------------

Coccomyxa_peltigerae    ----------------------------------------------------
Coccomyxa_chodatii      ----------------------------------------------------
C2003ILL6A              CGACGAGAGGATCCGATCAATAGACCGGGGAGAGCTCGTCGGGGGTGGCG 1648
Coccomyxa_sp_flensburg  ----------------------------------------------------
Coccomyxa_sp_CPCC       ----------------------------------------------------
Coccomyxa_glaronensis   ----------------------------------------------------
Chlamydomonas_sp        ----------------------------------------------------

Coccomyxa_peltigerae    ----------------------------------------------------
Coccomyxa_chodatii      ----------------------------------------------------
C2003ILL6A              GTAGTAGTTGCTGGAGCAATCCTGTCAATGGCTGAAACGAAGTTTCTTGC 1698
Coccomyxa_sp_flensburg  ----------------------------------------------------
Coccomyxa_sp_CPCC       ----------------------------------------------------
Coccomyxa_glaronensis   ----------------------------------------------------
Chlamydomonas_sp        ----------------------------------------------------

Coccomyxa_peltigerae    ----------------------GCCTGCGGCTTAATTTGACTCAACACG 1204
Coccomyxa_chodatii      ----------------------GCCTGCGGCTTAATTTGACTCAACACG 1204
C2003ILL6A              CTCGCCATCCGGAGTGTTCGGGAGCCTGCGGCTTAATTTGACTCAACACG 1748
Coccomyxa_sp_flensburg  ----------------------GCCTGCGGCTTAATTTGACTCAACACG 1198
Coccomyxa_sp_CPCC       ----------------------GCCTGCGGCTTAATTTGACTCAACACG 1199
Coccomyxa_glaronensis   ----------------------GCCTGCGGCTTAATTTGACTCAACACG 1198
Chlamydomonas_sp        ----------------------GCCTGCGGCTTAATTTGACTCAACACG 1096
                                              ******  *******************
```

Figure 3 (continued)

```
Cocconyxa_peltigerae      GGAAAACTTACCAGGTCCAGACATAGTGAGGATTGACAGATTGAGAGCTC 1254
Cocconyxa_chodatii        GGAAAACTTACCAGGTCCAGACATAGTGAGGATTGACAGATTGAGAGCTC 1254
C2003_LL6A                GGAAAACTTACCAGGTCCAGACATAGTGAGGATTGACAGATTGAGAGCTC 1798
Cocconyxa_sp_flensburg    GGAAAACTTACCAGGTCCAGACATAGTGAGGATTGACAGATTGAAAGCTC 1248
Cocconyxa_sp_CPCC         GGAAAACTTACCAGGTCCAGACATAGTGAGGATTGACAGATTGAGAGCTC 1249
Cocconyxa_glaronensis     GGAAAACTTACCAGGTCCAGACATAGTGAGGATTGACAGATTGAGAGCTC 1248
Chlamydomonas_sp          GGGAAACTTACCAGGTCCAGACACGGGGAGGATTGACAGATTGAGAGCTC 1146
                          ** ******************  * ***************** *****

Cocconyxa_peltigerae      TTTCTTGATTCTATGGGTGGTGGTGCATGGCCGTTCTTAGTTGGTGGGTT 1304
Cocconyxa_chodatii        TTTCTTGATTCTATGGGTGGTGGTGCATGGCCGTTCTTAGTTGGTGGGTT 1304
C2003_LL6A                TTTCTTGATTCTATGGGTGGTGGTGCATGGCCGTTCTTAGTTGGTGGGTT 1848
Cocconyxa_sp_flensburg    TTTCTTGATTCTATGGGTGGTGGTGCATGGCCGTTCTTAGTTGGTGGGTT 1298
Cocconyxa_sp_CPCC         TTTCTTGATTCTATGGGTGGTGGTGCATGGCCGTTCTTAGTTGGTGGGTT 1299
Cocconyxa_glaronensis     TTTCTTGATTCTATGGGTGGTGGTGCATGGCCGTTCTTAGTTGGTGGGTT 1298
Chlamydomonas_sp          TTTCTTGATTCTGTGGGTGGTGGTGCATGGCCGTTCTTAGTTGGTGGGTT 1196
                          ************ *************************************

Cocconyxa_peltigerae      GCCTTGTCAGGTTGATTCCGGTAACGAACGAGACCTCAGCCTGCTAACTA 1354
Cocconyxa_chodatii        GCCTTGTCAGGTTGATTCCGGTAACGAACGAGACCTCAGCCTGCTAACTA 1354
C2003_LL6A                GCCTTGTCAGGTTGATTCCGGTAACGAACGAGACCTCAGCCTGCTAACTA 1898
Cocconyxa_sp_flensburg    GCCTTGTCAGGTTGATTCCGGTAACGAACGAGACCTCAGCCTGCTAACTA 1348
Cocconyxa_sp_CPCC         GCCTTGTCAGGTTGATTCCGGTAACGAACGAGACCTCAGCCTGCTAACTA 1349
Cocconyxa_glaronensis     GCCTTGTCAGGTTGATTCCGGTAACGAACGAGACCTCAGCCTGCTAACTA 1348
Chlamydomonas_sp          GCCTTGTCAGGTTGATTCCGGTAACGAACGAGACCTCAGCCTGCTAAATA 1246
                          *********************************************** **

Cocconyxa_peltigerae      GTCACGATTGGTTCTTCCAGTCGGCCGGCTTCTTAGAGGGACTATTGGCG 1404
Cocconyxa_chodatii        GTCACCATTCGTTCTTCCAGTCGGCCCGACTTCTTAGACCCACTATTGGCG 1404
C2003_LL6A                GTCACGGTTGGTTTTTCCAGCCGGCGGACTTCTTAGAGGGACTATTGGCG 1948
Cocconyxa_sp_flensburg    GTCACGGCTGGATTCTCCAGCCGGCGGACTTCTTAGAGGGACTATTGGCG 1398
Cocconyxa_sp_CPCC         GTCACGGCTGGATTCTCCAGCCGGCGGACTTCTTAGAGGGACTATTGGCG 1399
Cocconyxa_glaronensis     GTCACGGCTGC-CCCGGCAGCCGGCGGACTTCTTAGAGGGACTATTGGCG 1397
Chlamydomonas_sp          GTCACGGGTACCTCGTGTACACGCTTGACTTCTTAGAGGGACTATTGGCG 1296
                          ******  *          *  **   * * *******************

Cocconyxa_peltigerae      ACTAGCCAATGGAAGTGTGAGGCAATAACAGGTCTGTGATGCCCTTAGAT 1454
Cocconyxa_chodatii        ACTAGCCAATGGAAGTGTGAGGCAATAACAGGTCTGTGATGCCCTTAGAT 1454
C2003_LL6A                ACTAGCCAATGGAAGTGTGAGGCAATAACAGGTCTGTGATGCCCTTAGAT 1998
Cocconyxa_sp_flensburg    ACTAGCCAATGGAAGTGTGAGGCAATAACAGGTCTGTGATGCCCTTAGAT 1448
Cocconyxa_sp_CPCC         ACTAGCCAATGGAAGTGTGAGGCAATAACAGGTCTGTGATGCCCTTAGAT 1449
Cocconyxa_glaronensis     ACTAGCCAATGGAAGTGTGAGGCAATAACAGGTCTGTGATGCCCTTAGAT 1447
Chlamydomonas_sp          TTTAGTCAATGGAAGTGTGAGGCAATAACAGGTCTGTGATGCCCTTAGAT 1346
                            *** *******************************************

Cocconyxa_peltigerae      GTTCTGGGCCGCACGCGCGCTACACTGATGCAGTCAACGAGCCTAGCCTT 1504
Cocconyxa_chodatii        GTTCTGGGCCGCACGCGCGCTACACTGATGCAATCAACGAGCCTAGCCTT 1504
C2003_LL6A                GTTCTGGGCCGCACGCGCGCTACACTGATGCAATCAACGAGCCTAGCCTT 2048
Cocconyxa_sp_flensburg    GTTCTGGGCCGCACGCGCGCTACACTGATGCGATCAACGAGCCTAGCCTT 1498
Cocconyxa_sp_CPCC         GTTCTGGGCCGCACGCGCGCTACACTGATGCGATCAACGAGCCTAGCCTT 1499
Cocconyxa_glaronensis     GTTCTGGGCCGCACGCGCGCTACACTGATGCGATCAACGAGCCTAGCCTT 1497
Chlamydomonas_sp          GTTCTGGGCCGCACGCGCGCTACACTGATGCATTCAACGAGCCTATCCTT 1396
                          *******************************   *********** ****

Cocconyxa_peltigerae      GGCCGACAGGTCCGGGTAATCTTTGAAACTGCATCGTGATGGGGATAGAT 1554
Cocconyxa_chodatii        GGCCGACAGGTCCGGGTAATCTTTGAAACTGCATCGTGATGGGGATAGAT 1554
C2003_LL6A                GGCCGAGAGGTCCGGGTAATCTTTGAAACTGCATCGTGATGGGGATAGAT 2098
Cocconyxa_sp_flensburg    GGCCGACAGGTCCGGGTAATCTTGCAAACCGCATCGTGATGGGGATAGAT 1548
Cocconyxa_sp_CPCC         CCCCACACGTCCCGGTAATCTTGCAAACCGCATCGTCATCGGATAGAT 1549
Cocconyxa_glaronensis     GGCCGACAGGTCCGGGTAATCTTGCAAACCGCATCGTGATGGGGATAGAT 1547
Chlamydomonas_sp          GACCGAGAGGTCCGGGTAATCTTTGAAACTGCATCGTGATGGGGATAGAT 1446
                           * **** ************ * * *** ******* *  ***********
```

Figure 3 (continued)

```
Coccomyxa_peltigerae    GATTGCAATTATTCATCTTCAACGAGGAATGCCTAGTAAGCGCGAGTCAT 1604
Coccomyxa_chodatii      GATTGCAATTATTCATCTTCAACGAGGAATGCCTAGTAAGCGCGAGTCAT 1604
C2003ILL6A              TATTGCAATTATTAATCTTCAACGAGGAATGCCTAGTAAGCGCGAGTCAT 2148
Coccomyxa_sp_flensburg  TATTGCAATTATTAATCTTCAACGAGGAATGCCTAGTAGGCGCGAGTCAT 1598
Coccomyxa_sp_CPCC       TATTGCAATTATTAATCTTCAACGAGGAATGCCTAGTAGGCGCGAGTCAT 1599
Coccomyxa_glaronensis   TATTGCAATTATTAATCTTCAACGAGGAATGCCTAGTAGGCGCGAGTCAT 1597
Chlamydomonas_sp        TATTGCAATTATTAGTCTTCAACGAGGAATGCCTAGTAAGCGCAAGTCAT 1496
                        *********** ********************** **** ******

Coccomyxa_peltigerae    CAGCTCGCGTTGATTACGTCCCTGCCCTTTGTACACACCGCCCGTCGCTC 1654
Coccomyxa_chodatii      CAGCTCGCGTTGATTACGTCCCTGCCCTTTGTACACACCGCCCGTCGCTC 1654
C2003ILL6A              CAGCTCGCGTTGATTACGTCCCTGCCCTTTGTACACACCGCCCGTCGCTC 2198
Coccomyxa_sp_flensburg  CAGCTCGCGTCGATTACGTCCCTGCCCTTTGTACACACCGCCCGTCGCTC 1648
Coccomyxa_sp_CPCC       CAGCTCGCGTCGATTACGTCCCTGCCCTTTGTACACACCGCCCGTCGCTC 1649
Coccomyxa_glaronensis   CAGCTCGCGTCGATTACGTCCCTGCCCTTTGTACACACCGCCCGTCGCTC 1647
Chlamydomonas_sp        CAGCTTGCGTTGATTACGTCCCTGCCCTTTGTACACACCGCCCGTCGCTC 1546
                        ***** **** ***************************************

Coccomyxa_peltigerae    CTACCGATTGGGTGTGCTGGTGAAGCGTTCGGATTGGCGGCAGTGCGCGG 1704
Coccomyxa_chodatii      CTACCGATTGGGTGTGCTGGTGAAGCGTTCGGATTGGCGGCAGTGCGCGG 1704
C2003ILL6A              CTACCGATTGGGTGTGCTGGTGAAGCGTTCGGATTGGCGGCTTCAGGCGG 2248
Coccomyxa_sp_flensburg  CTACCGATTGGGTGTGCTGGTGAAGCGTTCGGATTGGCGGCCTCCGGCGG 1698
Coccomyxa_sp_CPCC       CTACCGATTGGGTCTCCTCGTGAAGCGTTCCGATTGGCCCCCTCCCGCGG 1699
Coccomyxa_glaronensis   CTACCGATTGGGTGTGCTGGTGAAGCGTTCGGATTGGCGGCCTCCGGCGG 1697
Chlamydomonas_sp        CTACCGATTGGG-------------------------------------- 1558
                        ************

Coccomyxa_peltigerae    TTCGCCGCTCGCTGCAGCCGAGAAGTTCGTTAAACCCTCCCACCTAGAGG 1754
Coccomyxa_chodatii      TTCGCCGCTCGCTGCAGCCGAGAAGTTCGTTAAACCCTCCCACCTAGAGG 1754
C2003ILL6A              TTCGCCGCCCGATGCAGCCGAGAAGTTCGTTAAACCCTCCCACCTAGAGG 2298
Coccomyxa_sp_flensburg  TTCGCCGCTGGGAGCAGCCGAGAAGTTCGTTAAACCCTCCCACCTAGAGG 1748
Coccomyxa_sp_CPCC       TTCGCCGCTGGGAGCAGCCGAGAAGTTCGTTAAACCCTCCCACCTAGAGG 1749
Coccomyxa_glaronensis   TTCGCCGCTGGGAGCAGCCGAGAAGTTCGTTAAACCCTCCCACCTAGAGG 1747
Chlamydomonas_sp        --------------------------------------------------

Coccomyxa_peltigerae    AAGGAGAAGTCGTAACAAGGTTTCCGTAG--------------------- 1783
Coccomyxa_chodatii      AAGGAGAAGTCGTAACAAGGTTTCCGTAG--------------------- 1783
C2003ILL6A              AAGGAGAAGTCGTAACAAGGTTTCCGTAGAAGAATACTGTTTGTTAACAC 2348
Coccomyxa_sp_flensburg  AAGGAGAAGTCGTAACAAGGTTTCCGTAGG-------------------- 1778
Coccomyxa_sp_CPCC       AAGGAGAAGTCGTAACAAGGTTTCCGTAGGTGAACCTGCRGAAGGATC-- 1797
Coccomyxa_glaronensis   AAGGAGAAGTCGTAACAAGGTTTCCGTAGGTGAACCTGCRGAAGGATCAA 1797
Chlamydomonas_sp        --------------------------------------------------

Coccomyxa_peltigerae    ------
Coccomyxa_chodatii      ------
C2003ILL6A              CGTGCG 2354
Coccomyxa_sp_flensburg  ------
Coccomyxa_sp_CPCC       ------
Coccomyxa_glaronensis   ------
Chlamydomonas_sp        ------
```

Figure 3 (continued)

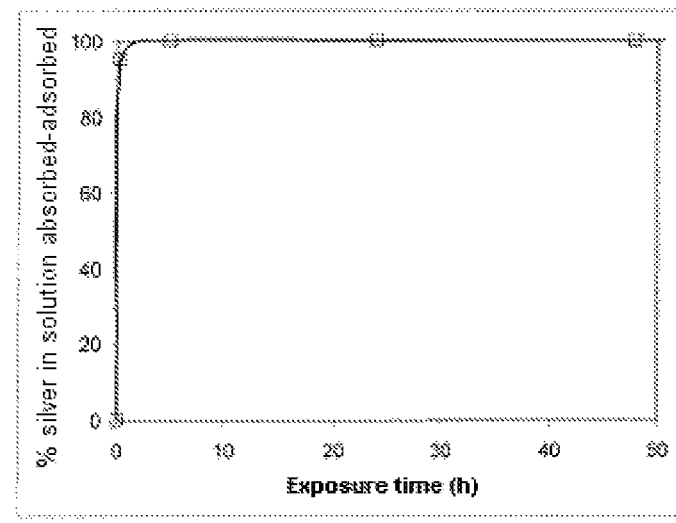
A
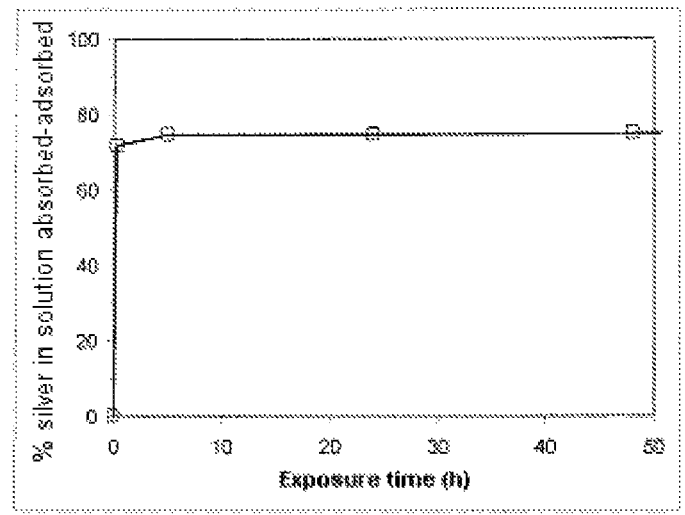
B
Figure 6

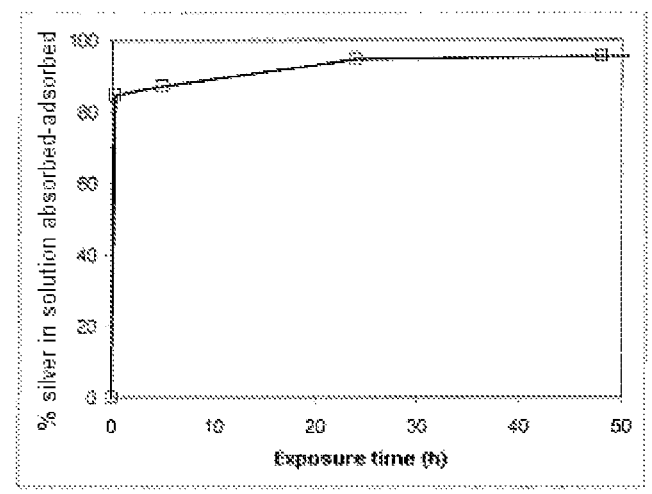
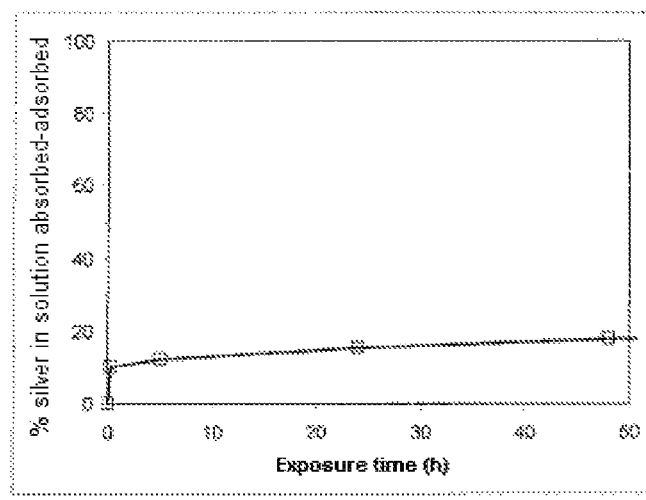
Figure 7

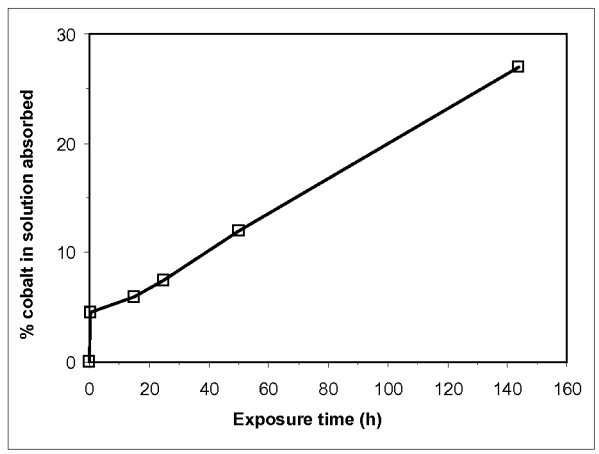
A
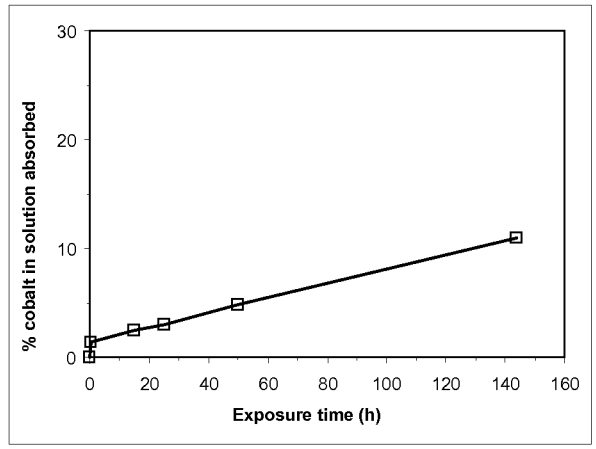
B
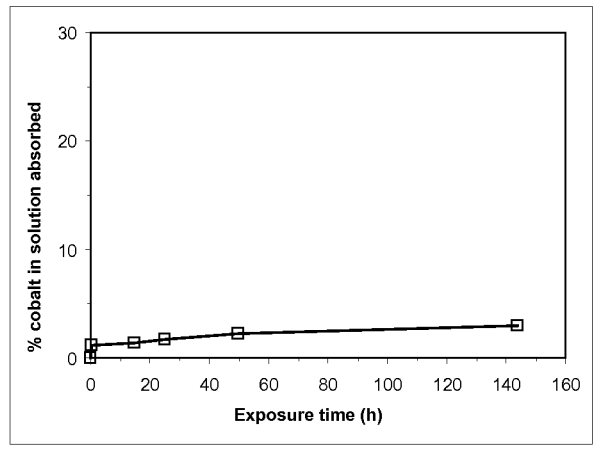
C
Figure 8

SEQUENCE LISTING

```
<160> NUMBER OF SEQ ID NOS: 13

<210> SEQ ID NO 1
<211> LENGTH: 4065
<212> TYPE: DNA
<213> ORGANISM: Coccomyxa actinabiotis
<220> FEATURE:
<221> NAME/KEY: rRNA
<222> LOCATION: (1)..(4065)
<220> FEATURE:
<221> NAME/KEY: misc_feature
<222> LOCATION: (3043)..(3043)
<223> OTHER INFORMATION: n = a, c, g, or t
<220> FEATURE:
<221> NAME/KEY: misc_feature
<222> LOCATION: (3195)..(3195)
<223> OTHER INFORMATION: n = a, c, g, or t
<220> FEATURE:
<221> NAME/KEY: misc_feature
<222> LOCATION: (4013)..(4016)
<223> OTHER INFORMATION: n = a, c, g, or t

<400> SEQUENCE: 1
cgacaatctg gttgatcctg ccagtagtca tatgcttgtc tcaaagatta agccatgcat      60
gtctaagtat aaactgcttt atactgtgaa actgcgaatg gctcattaaa tcagttatag     120
tttatttgat ggtaccttgc tactcggata accgtagtaa ttctagagct aatacgtgcg     180
taaatcccga cttctggaag ggacgtattt attagataaa aggccgaccg gactctgtcc     240
gactcgcggt gaatcatgat aactccacgg atcgcatggc ctcgagccgg cgatgtttca     300
ttcaaatttc tgccctatca actttcgacg gtaaggtatt ggcttaccgt ggtggtaacg     360
```

```
ggtgacggag gattagggtt cgattccgga gagggagcct gagaaacggc taccacatcc    420
aaggaaggca gcaggcgcgc aaattaccca atcttgacac aaggaggtag tgacaataaa    480
taacaatacc ggggttttc aactctggta attggaatga gtacaatcta aaccccttaa    540
cgaggatcaa ttggagggca agtctggtgc cagcagccgc ggtaattcca gctccaatag    600
cgtatattta agttgttgca gttaaaaagc tcgtagttgg atttcgggcg ggctcggccg    660
gtccgccgtt cggtgtgcac tgaccgagcc cgtcttgttg ccggggacgg gctcctgggc    720
ttaactgtcc gggactcgga gtcggcgagg ttactttgag taaattagag tgttcaaagc    780
aggcctacgc tctgaataca ttagcatgga ataacacgaa taggactctg gcctatcttg    840
ttggtctgtg gaccggagt aatgattaag agggacagtc gggggcattc gtatttcatt    900
gtcagaggtg aaattcttgg atttatgaaa gacgaactac tgcgaaagca tttgccaagg    960
atgttttcat taatcaagaa cgaaagttgg gggctcgaag acgattagat accgtcctag   1020
tctcaaccat aaacgatgcc gactaggat tggcgggcgt tcttttgatg acctcgccag   1080
caccttatga gaaatcaaag ttttttgggtt ccggggggag tatggtcgca aggctgaaac   1140
ttaaaggaat tgacgaagg gcaccaccag gcgtggaatg ttcatggctt tgcgcctcag   1200
agggatgctt taacgagtat ccctagtgcc tggtttcagg accaggcgca acaccgtcca   1260
attgcgggga ctccctaaag ctcgtgcaca ccaagcggtg aggggaaacc ccatcgtggc   1320
caggccaatc acctgggtaa ggtaacagtg gcgcgggatg aaggcgcagt aatgtgcctg   1380
aaatgggtga tccgcagcca agtcctacag agcccggcct gccgggttc cacggatgca   1440
gctcacagac taaatggcgg tgggtgtgat gcaatcattt aggaaacaca cgttcaggaa   1500
ttcaagacaa agaattgtgg attgtgaaca tgtgaatttg tcaaataaat gattgtaacc   1560
atgcttaaga tatagtcgga ccacctcgaa agaggcaccg acgagaggat ccgatcaata   1620
gaccggggag agctcgtcgg gggtggcggt agtagttgct ggagcaatcc tgtcaatggc   1680
tgaaacgaag tttcttgcct cgccatccgg agtgttcggg agcctgcggc ttaatttgac   1740
tcaacacggg aaaacttacc aggtccagac atagtgagga ttgacagatt gagagctctt   1800
tcttgattct atgggtggtg gtgcatggcc gttcttagtt ggtgggttgc cttgtcaggt   1860
tgattccggt aacgaacgag acctcagcct gctaactagt cacggttggt ttttccagcc   1920
ggcggacttc ttagagggac tattggcgac tagccaatgg aagtgtgagg caataacagg   1980
tctgtgatgc ccttagatgt tctgggccgc acgcgcgcta cactgatgca atcaacgagc   2040
ctagccttgg ccgagaggtc cgggtaatct ttgaaactgc atcgtgatgg ggatagatta   2100
ttgcaattat taatcttcaa cgaggaatgc ctagtaagcg cgagtcatca gctcgcgttg   2160
attacgtccc tgcccttttgt acacaccgcc cgtcgctcct accgattggg tgtgctggtg   2220
aagcgttcgg attggcggct tcaggcggtt cgccgcccga tgcagccgag aagttcgtta   2280
aaccctccca cctagaggaa ggagaagtcg taacaaggtt tccgtagaag aatactgttt   2340
gttaacaccg tgcggaacac agctcttcct tgtgtgctag tggggccctg gagccctgcg   2400
acactgtcaa attgcctgga actcccgctt ggatgtagtc cggtgccacc gcttccgatt   2460
ggaaacagtc gggagcaccg tcgggaaagc cgacgggtac ggtaacagag cgccggatga   2520
gggacgatgg gcagccaagt cctaagtgcg caagcatatg gatgcagttc acagactaaa   2580
tggcagtggg ttcctcagcg ccgatcagaa gcagaggagc ttaagatata gtcggaccgc   2640
cccgtgaggg gagccggcag gaggatcccg gttcagcaac cggcgagaga gcctgtcggg   2700
agcggcctaa tagttggcgt ctgtcaacgg cacacgtggg cctgccgctc ggagtagtcg   2760
```

-continued

```
aggtgaacct gcggaaggat cattgcatcg atcaaacaca aaccgcgaac cacgtatccc    2820
cgctgggcgg ctcctctttt gttatatcga aggaaggccg aacagtgcgc ttgtccctga    2880
cccgggtcct cggcttcga ggctcggcag gtctggcggg ccggggagac ctctctccga     2940
tcctgacccg atcggatgac gtcttctgtc ggtcggcaaa accccaatc acaaccgaac     3000 gtaacgaagc ctgaagcaat cggcgtgctg tcatcagccg tcncgaaacc aatgacaact    3060
ctcaacaatg gatgtcttgg ctcccgtatc gatgaagaac gcagcgaaat gcgatacgta    3120
gtgtgaattg cagataatgt gaatcatcga atctttgaac gcaaattgca ctcgaggctc    3180
cggccaagag tatgnctgcc tcagcgtcgg ctcacccct cgcctcccct ttgtctccta     3240
ccgaacaagg aaggatggcg gacgtggcg tcccggtgaa ctttccttcg aaggacaacc     3300
gggtccgctg aagaccagag gctcgagcaa ggacccattc gggacaaaca gtctggtagg    3360
agcgtcgtct cagacctcat gcccgctgtc ggcccgggac tttgttggag gccggaaggc    3420
gctcctcggt tatggtaacc ggagctcttc atgaaatatt cgacctgagt tcaggcaagg    3480
gcacccgctg aacttaagca tatcaataag cggaggaaaa gaaactaacc aggattcccc    3540
tagtagcggc gagcgaaccg ggaagagccc aacttgaaaa tctccgtctg ccaggcggcg    3600
aatgtagtct agagaggcgt cctctgtggc gggtcgtgcc caagtcccctt ggaagggggc    3660 gtccgagagg gtgagaaccc cgtcggccac ggcctcagcc actccacgag gcgctttcgc    3720
agagtcgggt tgtttgggaa tgcagcccaa agcaggtggt aagtcccatc taaggctaaa    3780
tactgacggg agaccgatag cgaacaagta ccgcgaggga aagatgaaaa gaactttgaa    3840
aagagagtta aaaagtgcct gaaattgttg aggggaagg gattggaggt cgcgggtgcg    3900
cccaggcaaa cgccttttac gctaaaaggc tgaatgtgct gggcgctggt cagcgtcggt    3960
tagccgggcg ggacaacagc ggtctttgat cggccgcctc tgtcgcccgg ctnnnngagg    4020
aacgaagggt gctctggcga ttcgtcgacc tgcgctctca ggatg                   4065
```

<210> SEQ ID NO 2
<211> LENGTH: 25
<212> TYPE: DNA
<213> ORGANISM: Artificial Sequence
<220> FEATURE:
<223> OTHER INFORMATION: PCR primer

<400> SEQUENCE: 2
tcgacaatct ggttgatcct gccag                                          25

<210> SEQ ID NO 3
<211> LENGTH: 26
<212> TYPE: DNA
<213> ORGANISM: Artificial Sequence
<220> FEATURE:
<223> OTHER INFORMATION: PCR primer

<400> SEQUENCE: 3
ctccttggtc cgtgtttcaa gacggg                                         26

<210> SEQ ID NO 4
<211> LENGTH: 2354
<212> TYPE: DNA
<213> ORGANISM: Coccomyxa actinabiotis
<220> FEATURE:
<221> NAME/KEY: rRNA
<222> LOCATION: (1)..(2354)

<400> SEQUENCE: 4

```
cgacaatctg gttgatcctg ccagtagtca tatgcttgtc tcaaagatta agccatgcat      60
gtctaagtat aaaactgctt tatactgtga actgcgaatg gctcattaaa tcagttatag     120
tttatttgat ggtaccttgc tactcggata accgtagtaa ttctagagct aatacgtgcg     180
taaatcccga cttctggaag ggacgtattt attagataaa aggccgaccg gactctgtcc     240
gactcgcggt gaatcatgat aactccacgg atcgcatggc ctcgagccgg cgatgtttca     300
ttcaaatttc tgccctatca actttcgacg gtaaggtatt ggcttaccgt ggtggtaacg     360
ggtgacggag gattagggtt cgattccgga gagggagcct gagaaacggc taccacatcc     420
aaggaaggca gcaggcgcgc aaattaccca atcttgacac aaggaggtag tgacaataaa     480
taacaatacc ggggtttttc aactctggta attggaatga gtacaatcta aaccccttaa     540
cgaggatcaa ttggagggca agtctggtgc cagcagccgc ggtaattcca gctccaatag     600
cgtatattta agttgttgca gttaaaaagc tcgtagttgg atttcgggcg ggctcggccg     660
gtccgccgtt cggtgtgcac tgaccgagcc cgtcttgttg ccggggacgg gctcctgggc     720
ttaactgtcc gggactcgga gtcggcgagg ttactttgag taaattagag tgttcaaagc     780
aggcctacgc tctgaataca ttagcatgga ataacacgaa taggactctg cctatcttg      840 ttggtctgtg ggaccggagt aatgattaag agggacagtc gggggcattc gtatttcatt     900
gtcagaggtg aaattcttgg atttatgaaa gacgaactac tgcgaaagca tttgccaagg     960
atgttttcat taatcaagaa cgaaagttgg gggctcgaag acgattagat accgtcctag    1020
tctcaaccat aaacgatgcc gactaggat tggcgggcgt tcttttgatg acctcgccag     1080
caccttatga gaaatcaaag ttttgggtt ccgggggag tatggtcgca aggctgaaac      1140
ttaaaggaat tgacggaagg gcaccaccag gcgtggaatg ttcatggctt gcgcctcag     1200 agggatgctt taacgagtat ccctagtgcc tggtttcagg accaggcgca acaccgtcca    1260
attgcgggga ctccctaaag ctcgtgcaca ccaagcggtg aggggaaacc ccatcgtggc    1320
caggccaatc acctgggtaa ggtaacagtg gcgcgggatg aaggcgcagt aatgtgcctg    1380
aaatgggtga tccgcagcca agtcctacag agcccggcct gcccgggttc cacggatgca    1440
gctcacagac taaatggcgg tgggtgtgat gcaatcattt aggaaacaca cgttcaggaa    1500
ttcaagacaa agaattgtgg attgtgaaca tgtgaatttg tcaaataaat gattgtaacc    1560
atgcttaaga tatagtcgga ccacctcgaa agaggcaccg acgagaggat ccgatcaata    1620
gaccggggag agctcgtcgg gggtggcggt agtagttgct ggagcaatcc tgtcaatggc    1680
tgaaacgaag tttcttgcct cgccatccgg agtgttcggg agcctgcggc ttaatttgac    1740
tcaacacggg aaaacttacc aggtccagac atagtgagga ttgacagatt gagagctctt    1800
tcttgattct atgggtggtg gtgcatggcc gttcttagtt ggtgggttgc cttgtcaggt    1860
tgattccggt aacgaacgag acctcagcct gctaactagt cacggttggt ttttccagcc    1920
ggcggacttc ttagagggac tattggcgac tagccaatgg aagtgtgagg caataacagg    1980
tctgtgatgc ccttagatgt tctgggccgc acgcgcgcta cactgatgca atcaacgagc    2040
ctagccttgg ccgagaggtc cgggtaatct ttgaaactgc atcgtgatgg ggatagatta    2100
ttgcaattat taatcttcaa cgaggaatgc ctagtaagcg cgagtcatca gctcgcgttg    2160
attacgtccc tgccctttgt acacaccgcc cgtcgctcct accgattggg tgtgctggtg    2220
aagcgttcgg attggcggct tcaggcggtt cgccgcccga tgcagccgag aagttcgtta    2280
aaccctccca cctagaggaa ggagaagtcg taacaaggtt tccgtagaag aatactgttt    2340
gttaacaccg tgcg                                                      2354
```

<210> SEQ ID NO 5
<211> LENGTH: 1783
<212> TYPE: DNA
<213> ORGANISM: Coccomyxa peltigerae
<220> FEATURE:
<221> NAME/KEY: rRNA
<222> LOCATION: (1)..(1783)

<400> SEQUENCE: 5

| | | | | | | |
|---|---|---|---|---|---|---|
| tcgacaatct | ggttgatcct | gccagtagtc | atatgcttgt | ctcaaagatt | aagccatgca | 60 |
| tgtctaagta | taaactgctt | tatactgtga | aactgcgagt | ggctcgttaa | atcagttata | 120 |
| gtttatttga | tggtacctta | ctactcggat | aaccgtagta | attctagagc | taatacgtgc | 180 |
| ggaaatcccg | acttccggaa | gggacgtatt | tattagataa | aaggccgacc | gggcttgccc | 240 |
| gaaacgcggt | gaatcatgat | aactccacga | atcgcatggc | ctcagtgccg | gcgatgtttc | 300 |
| attcaaattt | ctgccctatc | aactttcgac | ggtaaggtat | tggcttaccg | tggtggtaac | 360 |
| gggtgacgga | ggattgggt | tcgattccgg | agagggagcc | tgagaaacgg | caaccacatc | 420 |
| caaggaaggc | agcaggcgcg | caaattaccc | aatcttgaca | caaggaggta | gtgacaatga | 480 |
| ataacaatac | cggggttttt | caactctggt | aattggaatg | agtacaatct | aaacccctta | 540 |
| acgaggatca | attggagggc | aagtctggtg | ccagcagccg | cggtaattcc | agctccaata | 600 |
| gcgtatattt | aagttgttgc | agttaaaaag | ctcgtagttg | gatttcgggc | gggcccggcc | 660 |
| ggtccgcctt | cgggtgtgca | ctgaccgggc | ccgtcatgtt | gccggggacg | ggctcctggg | 720 |
| cttcactgtc | cgggactcgg | agtcggcgag | gttactttga | gtaaattaga | gtgttcaaag | 780 |
| caggcctacg | ctctgaatac | attagcatgg | aataacacga | taggactctg | gcctatcttg | 840 |
| ttggtctgtg | ggaccggagt | aatgattaag | agggacagtc | gggggcattc | gtatttcatt | 900 |
| gtcagaggtg | aaattcttgg | atttatgaaa | gacgaactac | tgcgaaagca | tttgccaagg | 960 |
| atgttttcat | taatcaagaa | cgaaagttgg | gggctcgaag | acgattagat | accgtcctag | 1020 |
| tctcaaccat | aaacgatgcc | gactagggat | tggcggcgt | tcttttgatg | accccgccag | 1080 |
| caccttatga | gaaatcaaag | tttttgggtt | ccggggggag | tatggtcgca | aggctgaaac | 1140 |
| ttaaaggaat | tgacggaagg | gcaccaccag | gcgtggagcc | tgcggcttaa | tttgactcaa | 1200 |
| cacgggaaaa | cttaccaggt | ccagacatag | tgaggattga | cagattgaga | gctctttctt | 1260 |
| gattctatgg | gtggtggtgc | atggccgttc | ttagttggtg | ggttgccttg | tcaggttgat | 1320 |
| tccggtaacg | aacgagacct | cagcctgcta | actagtcacg | attggttctt | ccagtcggcc | 1380 |
| ggcttcttag | agggactatt | ggcgactagc | caatggaagt | gtgaggcaat | aacaggtctg | 1440 |
| tgatgccctt | agatgttctg | gccgcacgc | gcgctacact | gatgcagtca | acgagcctag | 1500 |
| ccttggccga | caggtccggg | taatctttga | aactgcatcg | tgatggggat | agatgattgc | 1560 |
| aattattcat | cttcaacgag | gaatgcctag | taagcgcgag | tcatcagctc | gcgttgatta | 1620 |
| cgtccctgcc | ctttgtacac | accgcccgtc | gctcctaccg | attgggtgtg | ctggtgaagc | 1680 |
| gttcggattg | gcggcagtgc | gcggttcgcc | gctcgctgca | gccgagaagt | tcgttaaacc | 1740 |
| ctcccaccta | gaggaaggag | aagtcgtaac | aaggtttccg | tag | | 1783 |

<210> SEQ ID NO 6
<211> LENGTH: 1783
<212> TYPE: DNA
<213> ORGANISM: Unknown
<220> FEATURE:
<223> OTHER INFORMATION: Coccomyxa chodatii strain SAG 216-2
<220> FEATURE:
<221> NAME/KEY: rRNA

```
<222> LOCATION: (1)..(1783)

<400> SEQUENCE: 6
tcgacaatct ggttgatcct gccagtagtc atatgcttgt ctcaaagatt aagccatgca        60
tgtctaagta taaactgctt tatactgtga aactgcgaat ggctcattaa atcagttata       120
gtttatttga tggtacctta ctactcggat aaccgtagta attctagagc taatacgtgc       180
ggaaatcccg acttctggaa gggacgtatt tattagataa aaggccgacc gggcttgccc       240
gaaacgcggt gaatcatgat aactccacga atcgcatggc ctcagtgccg gcgatgtttc       300
attcaaattt ctgccctatc aactttcgac ggtaaggtat tggcttaccg tggtggtaac       360
gggtgacgga ggattagggt tcgattccgg agagggagcc agagaaacgg ctaccacatc       420
caaggaaggc agcaggcgcg caaattaccc aatcttgaca caaggaggta gtgacaataa       480
ataacaatac cggggttttt caactctggt aattggaatg agtacaatct aaacccctta       540
acgaggatca attggagggc aagtctggtg ccagcagccg cggtaattcc agctccaata       600
gcgtatattt aagttgttgc agttaaaaag ctcgtagttg gatctcgggc gggcccggcc       660
ggtccgcctt cgggtgtgca ctgaccgggc ccgtcttgtt gccggggacg ggctcctggg       720
cttcactgtc cgggactcgg agtcggcgag gttactttga gtaaattaga gtgttcaaag       780
caggcctacg ctctgaatac attagcatgg aataacacga taggactctg cctatcttg       840
ttggtctgtg gaccggagt gatgattaag agggacagtc gggggcattc gtatttcatt       900
gtcagaggtg aaattcttgg atttatgaaa gacgaactac tgcgaaagca tttgccaagg       960
atgttttcat taatcaagaa cgaaagttgg gggctcgaag acgattagat accgtcctag      1020
tctcaaccat aaacgatgcc gactaggat tggcgggcgt tcttttgatg accccgccag      1080
caccttatga gaaatcaaag ttttgggtt ccgggggag tatggtcgca aggctgaaac      1140
ttaaaggaat tgacggaagg gcaccaccag gcgtggagcc tgcggcttaa tttgactcaa      1200
cacgggaaaa cttaccaggt ccagacatag tgaggattga cagattgaga gctctttctt      1260
gattctatgg gtggtggtgc atggccgttc ttagttggtg ggttgccttg tcaggttgat      1320
tccggtaacg aacgagacct cagcctgcta actagtcacg attggttctt ccagtcggcc      1380
gacttcttag agggactatt ggcgactagc caatggaagt gtgaggcaat aacaggtctg      1440
tgatgccctt agatgttctg ggccgcacgc gcgctacact gatgcaatca acgagcctag      1500
ccttggccga caggtccggg taatctttga aactgcatcg tgatgggat agatgattgc      1560
aattattcat cttcaacgag gaatgcctag taagcgcgag tcatcagctc gcgttgatta      1620
cgtccctgcc ctttgtacac accgcccgtc gctcctaccg attgggtgtg ctggtgaagc      1680
gttcggattg gcggcagtgc gcggttcgcc gctcgctgca gccgagaagt tcgttaaacc      1740
ctcccaccta gaggaaggag aagtcgtaac aaggtttccg tag                        1783

<210> SEQ ID NO 7
<211> LENGTH: 1778
<212> TYPE: DNA
<213> ORGANISM: Coccomyxa Flensburg
<220> FEATURE:
<221> NAME/KEY: rRNA
<222> LOCATION: (1)..(1778)

<400> SEQUENCE: 7
acctggttga tcctgccagt agtcatatgc ttgtctcaaa gattaagcca tgcatgtcta        60
agtataaact gatttatact gtgaaactgc gaatggctct taaatcagt tatagtttat       120
ttgatggtac cttgctactc ggataaccgt agtaattcta gagctaatac gtgcggaaat       180
```

```
cccgactcct ggaagggacg tatttattag ataaaaggcc gaccggactc cgtccgactc    240
gcggtgaatc atgataactc cacgaatcgc atggcccagc gccggcgatg tttcattcaa    300
atttctgccc tatcaacttt cgacggtaag gtattggctt accgtggtgg taacgggtga    360
cggaggatta gggttcgatt ccggagaggg agcctgagaa acggctacca catccaagga    420
aggcagcagg cgcgcaaatt acccaatctt gacacaagga ggtagtgaca ataataaca     480 ataccggggt tattcaactc tggtaattgg aatgagtaca atctaaaccc cttaatgagg    540
atcaattgga gggcaagtct ggtgccagca gccccggtaa ttccagctcc aatagcgtat    600
atttaagttg ttgcagttaa aaagctcgta gttggatttc gggcgggccc ggccggtccg    660
cctcacggtg tgcactgacc gggcccgtcc tgctgccggg gacgggctcc tgggcttcac    720
tgtccgggac tcggagtcgg cgaggttact ttgagtaaat tagagtgttc aaagcaggca    780
tccgccttga atacgttagc atggaataac acgataggac tctggcctat cttgttggtc    840
tgtgggaccg gagtaatgat taagagggac agtcgggggc attcgtattt cattgtcaga    900
ggtgaaattc ttggatttat gaaagacgaa ctactgcgaa agcatttgcc aaggatgttt    960
tcattaatca agaacgaaag ttgggggctc gaagacgatt agataccgtc ctagtctcaa   1020
ccataaacga tgccgactag ggattggcgg gcgttctatt gatgacccg ccagcaccttt   1080 atgagaaatc aaagttttttg ggttccgggg ggagtatggt cgcaaggctg aaacttaaag   1140
gaattgacgg aagggcacca ccaggcgtgg agcctgccgc ttaatttgac tcaacacggg   1200
aaaacttacc aggtccagac atagtgagga ttgacagatt gaaagctctt tcttgattct   1260
atgggtggtg gtgcatggcc gttcttagtt ggtgggttgc cttgtcaggt tgattccggt   1320
aacgaacgag acctcagcct gctaactagt cacggctgga ttctccagcc ggcggacttc   1380
ttagagggac tattggcgac tagccaatgg aagtgtgagg caataacagg tctgtgatgc   1440
ccttagatgt tctgggccgc acgcgcgcta cactgatgcg atcaacgagc ctagccttgg   1500
ccgacaggtc cgggtaatct tgcaaaccgc atcgtgatgg ggatagatta ttgcaattat   1560
taatcttcaa cgaggaatgc ctagtaggcg cgagtcatca gctcgcgtcg attacgtccc   1620
tgccctttgt acacaccgcc cgtcgctcct accgattggg tgtgctggtg aagcgttcgg   1680
attggcggcc tccggcggtt cgccgctggg agcagccgag aagttcgtta aaccctccca   1740
cctagaggaa ggagaagtcg taacaaggtt tccgtagg                            1778

<210> SEQ ID NO 8
<211> LENGTH: 1797
<212> TYPE: DNA
<213> ORGANISM: Coccomyxa glaronensis

<400> SEQUENCE: 8
aacctggttg atcctgccag tagtcatatg cttgtctcaa agattaagcc atgcatgtct     60
aagtataaac tgctttatac tgtgaaactg cgaatggctc attaaatcag ttatagttta    120
tttgatggta ccttgctact cggataaccg tagtaattct agagctaata cgtgcggaaa    180
tcccgactcc tggaagggac gtattttatta gataaaaggc cgaccggact cgtccgactc    240
gcggtgaatc atgataactc cacgaatcgc atggcccagc gccggcgatg tttcattcaa    300
atttctgccc tatcaacttt cgacggtaag gtattggctt accgtggtgg taacgggtga    360
cggaggatta gggttcgatt ccggagaggg agcctgagaa acggctacca catccaagga    420
aggcagcagg cgcgcaaatt acccaatctt gacacaagga ggtagtgaca ataataaca     480 ataccggggt ttttcaactc tggtaattgg aatgagtaca atctaaaccc cttaacgagg    540
```

-continued

```
atcaattgga gggcaagtct ggtgccagca gccgcggtaa ttccagctcc aatagcgtat      600
atttaagttg ttgcagttaa aaagctcgta gttggatttc gggcgggccc ggccggtccg      660
cctcacggtg tgcactgacc gggcccgtcc tgctgccggg acgggctcc tgggcttcac       720 tgtccgggac tcggagtcgg cgaggttact ttgagtaaat tagagtgttc aaagcaggca      780
tccgccttga atacgttagc atggaataac acgataggac tctggcctat cttgttggtc      840
tgtgggaccg gagtaatgat taagagggac agtcggggc attcgtattt cattgtcaga      900
ggtgaaattc ttggatttat gaaagacgaa ctactgcgaa agcatttgcc aaggatgttt      960
tcattaatca agaacgaaag ttgggggctc gaagacgatt agataccgtc ctagtctcaa     1020
ccataaacga tgccgactag ggattggcgg gcgttctatt gatgacccg ccagcacctt      1080 atgagaaatc aaagttttg ggttccgggg ggagtatggt cgcaaggctg aaacttaaag      1140
gaattgacgg aagggcacca ccaggcgtgg agcctgcggc ttaatttgac tcaacacggg     1200
aaaacttacc aggtccagac atagtgagga ttgacagatt gagagctctt tcttgattct     1260
atgggtggtg gtgcatggcc gttcttagtt ggtgggttgc cttgtcaggt tgattccggt     1320
aacgaacgag acctcagcct gctaactagt cacggctgcc ccggcagccg gcggacttct     1380
tagagggact attggcgact agccaatgga agtgtgaggc aataacaggt ctgtgatgcc     1440
cttagatgtt ctgggccgca cgcgcgctac actgatgcga tcaacgagcc tagccttggc     1500
cgacaggtcc gggtaatctt gcaaaccgca tcgtgatggg gatagattat tgcaattatt     1560
aatcttcaac gaggaatgcc tagtaggcgc gagtcatcag ctcgcgtcga ttacgtccct     1620
gccctttgta cacaccgccc gtcgctccta ccgattgggt gtgctggtga agcgttcgga     1680
ttggcggcct ccggcggttc gccgctggga gcagccgaga agttcgttaa accctcccac     1740
ctagaggaag gagaagtcgt aacaaggttt ccgtaggtga acctgcrgaa ggatcaa        1797
```

<210> SEQ ID NO 9
<211> LENGTH: 1797
<212> TYPE: DNA
<213> ORGANISM: Unknown
<220> FEATURE:
<223> OTHER INFORMATION: Coccomyxa sp. strain CPCC 508
<220> FEATURE:
<221> NAME/KEY: rRNA
<222> LOCATION: (1)..(1797)

<400> SEQUENCE: 9

```
wacctggttg atcctgccag tagtcatatg cttgtctcaa agattaagcc atgcatgtct       60
aagtataaac tgctttatac tgtgaaactg cgaatggctc attaaatcag ttatagttta      120
tttgatggta ccttgctact cggataaccg tagtaattct agagctaata cgtgcggaaa      180
tcccgactcc tggaagggac gtatttatta gataaaaggc cgaccggact ctgtccgact      240
cgcggtgaat catgataact ccacgaatcg catggcccag cgccggcgat gtttcattca      300
aatttctgcc ctatcaactt cgacggtaa ggtattggct taccgtggtg gtaacgggtg       360
acggaggatt agggttcgat tccggagagg agcctgaga acggctacc acatccaagg        420 aaggcagcag gcgcgcaaat tacccaatct tgacacaagg aggtagtgac aataaataac      480
aataccgggg ttattcaact ctggtaattg gaatgagtac aatctaaacc ccttaacgag      540
gatcaattgg agggcaagtc tggtgccagc agccgcggta attccagctc caatagcgta      600
tatttaagtt gttgcagtta aaagctcgt agttggattt cgggcgggcc cggccggtcc       660
gcctcacggt gtgcactgac cgggcccgtc ctgctgccgg gacgggctc ctgggcttca      720
```

```
ctgtccggga ctcggagtcg gcgaggttac tttgagtaaa ttagagtgtt caaagcaggc         780
atccgccttg aatacgttag catggaataa cacgatagga ctctggccta tcttgttggt         840
ctgtgggacc ggagtaatga ttaagaggga cagtcggggg cattcgtatt tcattgtcag         900
aggtgaaatt cttggattta tgaaagacga actactgcga aagcatttgc caaggatgtt         960
ttcattaatc aagaacgaaa gttggggggct cgaagacgat tagataccgt cctagtctca      1020
accataaacg atgccgacta gggattggcg gcgttctat tgatgacccc gccagcacct         1080
tatgagaaat caaagttttt gggttccggg gggagtatgg tcgcaaggct gaaacttaaa      1140
ggaattgacg aagggcacc accaggcgtg gagcctgcgg cttaatttga ctcaacacgg       1200
gaaaacttac caggtccaga catagtgagg attgacagat tgagagctct ttcttgattc       1260
tatgggtggt ggtgcatggc cgttcttagt tggtgggttg ccttgtcagg ttgattccgg       1320
taacgaacga gacctcagcc tgctaactag tcacggctgg attctccagc cggcggactt       1380
cttagaggga ctattggcga ctagccaatg gaagtgtgag gcaataacag gtctgtgatg       1440
cccttagatg ttctgggccg cacgcgcgct acactgatgc gatcaacgag cctagccttg       1500
gccgacaggt ccgggtaatc ttgcaaaccg catcgtgatg gggatagatt attgcaatta     1560
ttaatcttca acgaggaatg cctagtaggc gcgagtcatc agctcgcgtc gattacgtcc       1620 ctgcccttg tacacaccgc ccgtcgctcc taccgattgg gtgtgctggt gaagcgttcg        1680
gattggcggc ctccggcggt tcgccgctgg gagcagccga gaagttcgtt aaaccctccc       1740
acctagagga aggagaagtc gtaacaaggt ttccgtaggt gaacctgcrg aaggatc           1797

<210> SEQ ID NO 10
<211> LENGTH: 1558
<212> TYPE: DNA
<213> ORGANISM: Unknown
<220> FEATURE:
<223> OTHER INFORMATION: Chlamydomonas sp. CCMP681
<220> FEATURE:
<221> NAME/KEY: rRNA
<222> LOCATION: (1)..(1558)

<400> SEQUENCE: 10
gctcattaat cagttatagt ttatttgatg gtacctttac tcggataacc gtagtaattc          60
tagagctaat acgtgcgtaa atcccgactt ctggaaggga cgtatttatt agataaaagg      120
ccagccgggc ttgcccgacc ttaggcgaat catgataact tcacgaatcg catggccttg      180
tgccggcgat gtttcattca aatttctgcc ctatcaactt tcgatggtag atagaggcc        240 taccatggtg gtaacgggtg acggaggatt agggttcgat tccggagagg gagcctgaga    300
aacggctacc acatccaagg aaggcagcag gcgcgcaaat tacccaatcc cgacacgggg    360
aggtagtgac aataaataac aataccgggc atctttgtct ggtaattgga atgagtacaa      420
tgtaaatatc ttaacgagta tccattggag ggcaagtctg gtgccagcag ccgcggtaat     480
tccagctcca atagcgtata tttaagttgt tgcagttaaa aagctcgtag ttggatttcg      540
ggtgggttgc agtggtctgc cactggtatg tactgctgcg gctcaccttt ctgctgggga      600
cgggctcctg ggcttaactg tctgggactc ggaatcagcg aagtgacctt gagcaaaagt     660
gagtgttcaa agcaagccta cgctctgaaa catttagcat gggatcacac gataggactc      720
tggcctatct tgttggtctg taggaccgga gtaatgatta gagggacag tcgggggcat       780 tcgtatttca ttgtcagagg tgaaattctt ggatttatga agacgaaca tctgcgaaag      840 catttgccaa ggatgttttc attgatcaag aacgaaagtt gggggctcga agacgattag      900
ataccgtcgt agtctcaacc ataaacgatg ccgactaggg attggcaggt gtttcgttga     960
```

```
tgaccctgcc agcaccttat gagaaatcaa agttttgggg ttccgggggg agtatggtcg      1020
caaggctgaa acttaaagga attgacggaa gggcaccacc aggcgtggag cctgcggctt      1080
aatttgactc aacacgggga aacttaccag gtccagacac ggggaggatt gacagattga      1140
gagctctttc ttgattctgt gggtggtggt gcatggccgt tcttagttgg tgggttgcct      1200
tgtcaggttg attccggtaa cgaacgagac ctcagcctgc taaatagtca cgggtacctc      1260
gtgtacacgc ttgacttctt agagggacta ttggcgttta gtcaatggaa gtgtgaggca      1320
ataacaggtc tgtgatgccc ttagatgttc tgggccgcac gcgcgctaca ctgatgcatt      1380
caacgagcct atccttgacc gagaggtccg ggtaatcttt gaaactgcat cgtgatgggg      1440
atagattatt gcaattatta gtcttcaacg aggaatgcct agtaagcgca agtcatcagc      1500
ttgcgttgat tacgtccctg ccctttgtac acaccgcccg tcgctcctac cgattggg       1558
```

<210> SEQ ID NO 11
<211> LENGTH: 761
<212> TYPE: DNA
<213> ORGANISM: Coccomyxa actinabiotis
<220> FEATURE:
<221> NAME/KEY: rRNA
<222> LOCATION: (1)..(761)
<223> OTHER INFORMATION: ITS1-5.8S rRNAITS2 sequence
<220> FEATURE:
<221> NAME/KEY: misc_feature
<222> LOCATION: (305)..(305)
<223> OTHER INFORMATION: n is a, c, g, or t
<220> FEATURE:
<221> NAME/KEY: misc_feature
<222> LOCATION: (457)..(457)
<223> OTHER INFORMATION: n is a, c, g, or t

<400> SEQUENCE: 11

```
ggcctgccgc tcggagtagt cgaggtgaac ctgcggaagg atcattgcat cgatcaaaca       60
caaaccgcga accacgtatc cccgctgggc ggctcctctt ttgttatatc gaaggaaggc      120
cgaacagtgc gcttgtccct gacccgggtc ctcggctttc gaggctcggc aggtctggcg      180
ggccggggag acctctctcc gatcctgacc cgatcggatg acgtcttctg tcggtcggca      240 aaaccccccaa tcacaaccga acgtaacgaa gcctgaagca atcggcgtgc tgtcatcagc      300
cgtcncgaaa ccaatgacaa ctctcaacaa tggatgtctt ggctcccgta tcgatgaaga      360
acgcagcgaa atgcgatacg tagtgtgaat tgcagataat gtgaatcatc gaatctttga      420
acgcaaattg cactcgaggc tccggccaag agtatgnctg cctcagcgtc ggctcacccc      480
ctcgcctccc ctttgtctcc taccgaacaa ggaaggatgg cggacgtggc ggtcccggtg      540
aactttcctt cgaaggacaa ccgggtccgc tgaagaccag aggctcgagc aaggacccat      600
tcgggacaaa cagtctggta ggagcgtcgt ctcagacctc atgcccgctg tcggcccggg      660
actttgttgg aggccggaag gcgctcctcg gttatggtaa ccggagctct tcatgaaata      720
ttcgacctga gttcaggcaa gggcacccgc tgaacttaag c                         761
```

<210> SEQ ID NO 12
<211> LENGTH: 617
<212> TYPE: DNA
<213> ORGANISM: Unknown
<220> FEATURE:
<223> OTHER INFORMATION: Coccomyxa chodatii strain SAG 216-2
<220> FEATURE:
<221> NAME/KEY: rRNA
<222> LOCATION: (1)..(617)
<223> OTHER INFORMATION: ITS1-5.8S rRNAITS2 sequence

<400> SEQUENCE: 12

```
gtgaacctgc ggaaggatca ttgcatcgat caaacacaca ccgcgaaccc acgtatcccc      60
gcgggcggct cctttcctt cgtgagaagt cagccggctg tgcgcttgtc cctgccgcaa      120
caccggcagg tctggcggc cggggaggcc gctctcctct aaccgggaga ggacctaatc      180
cggtcggcaa aaccccaatc gatcccaacc agaaaccgcc cgaagacgtc gacggctgtc      240
tgacagccgt ctccaaccaa agacaactct caacaacgga tatcttggct cccgtatcga      300
tgaagaacgc agcgaaatgc gatacgtagt gtgaattgca gataatgtga atcatcgaat      360
ctttgaacgc aaattgcact cgaggctccg gccgagagta tgtctgcctc agcgtcggct      420
ttaccctcac ccctctttca agaggcgtgg acctggccgt tccggttgac ttaaccgggt      480
ctgccgaaga acagaggctc taacgaggac ccaatcggga cgactgtctg gtaggtgacc      540
cgccagggat cgcatgccgc cgtcggcccg ggacctggtt gtaagccggc aggcaagaac      600
acccgctgaa cttaagc                                                    617

<210> SEQ ID NO 13
<211> LENGTH: 708
<212> TYPE: DNA
<213> ORGANISM: Unknown
<220> FEATURE:
<223> OTHER INFORMATION: Coccomyxa peltigerae strain SAG 216-5
<220> FEATURE:
<221> NAME/KEY: rRNA
<222> LOCATION: (1)..(708)
<223> OTHER INFORMATION: ITS1-5.8SrRNAITS2 sequence

<400> SEQUENCE: 13
gtgaacctgc ggaaggatca ttgcatcgat caaacacaaa ccgcgaaccc acgtatcccc      60
gcggccttct gtctttctct tcggggaaag agagccggcc gtgcgcttgt ccctgtccgg      120
ttccgcttcg gcggaaaggg caggtctagc gggctgggga ggccgctctc ccttaaccgg      180
gggagggcca aaacccggct ggcaaaaacc ccattcgatc caaaccagaa aataactga       240 agatccggac agctgttcaa gaacagccgt ctccaaccaa agacaactct caacaacgga      300
tatcttggct cccgtatcga tgaagaacgc agcgaaatgc gatacgtagt gtgaattgca      360
gataatgtga atcatcgaat ctttgaacgc aaattgcact cgaggctccg gccgagagta      420
tgtctgcctc agcgtcggct tcaccctcac ccctctccac cgagaggcgt ggacctggcc      480
gtcccggtta atgcaaccgg gtctgccgaa gaacagaggc tcgaacgagg acccaatcgg      540
gacaacagtc tggtaggtga cccgtcaggg atcgcatgcc gctgtcggcc cgggacctcg      600
ttgtaagccg gcaggaatcg gcggtcgctt tttttagaa aaaggagcgg ccgcacgaca      660 caccctttc gacctgagtt caggcaagaa cacccgctga acttaagc                   708
```

RADIORESISTANT ALGA OF THE *COCCOMYXA* GENUS

RELATED APPLICATIONS

The present application is a U.S. National Phase Application of International Application No. PCT/IB201/050589 (filed Feb. 11, 2011) which claims priority to French Application No. 1000578 (filed Feb, 12, 2010) which are hereby incorporated by reference in their entirety.

SEQUENCE LISTING SUBMISSION VIA EFS-WEB

A computer readable text file, entitled "045636-5205_SeqListing_08092012.txt," created on or about Aug. 7, 2012, with a file size of about 28 kb contains the sequence listing for this application and is hereby incorporated by reference in its entirety.

The invention relates to novel algae and to the use thereof for metal uptake from aqueous media, and in particular from radioactive media.

Radioactive effluents are produced mainly by nuclear power stations. They are mainly water from spent fuel storage pools, water from decontamination tanks, or else water from cooling circuits of nuclear plants, which ultimately contain radioactive compounds owing to the activation of inactive compounds by radiation, or to the release and dissolution of radioactive compounds. Other sources of radioactive effluents are nuclear medicine, research laboratories using radioactive materials, and also certain non-nuclear industries (for example extraction of rare earths).

Various physical and chemical methods are used to purify the effluents, in particular water, containing radioactive compounds. However, they have high operating and equipment costs, require heavy maintenance and generate large volumes of radioactive waste. Furthermore, their field of application is often limited. For example, ion exchange resins are used to maintain low conductivity in water from nuclear plants. They become loaded with radioactive ions and are stored while awaiting a suitable retreatment procedure when they are saturated, or stored under conditions using toxic or highly reactive compounds.

Moreover, biological methods exist which use, for example, bacteria, fungi, yeasts or plants to purify media contaminated (industrial effluents, natural media, etc.) with toxic products (nonradioactive or radioactive). These methods use living organisms to concentrate and assimilate polluting compounds and to make them less toxic (modification of the chemical form) or non-living biomass and also derivatives originating from living organisms to biosorb pollutants. The biological methods generally have a broader field of application than the physical and chemical methods. They do not require the addition of chemical reagents or products and generally enable less expensive treatment, hence their economic interest.

Plants in particular are good soil or water purifiers since they have an entire system of metabolites, proteins, enzymes, import mechanisms, membrane channels, internal structure, etc., which make them capable, as appropriate, of immobilizing toxic compounds, of chelating them outside or inside the plant, of incorporating them in more or less large amounts via specific or nonspecific import pathways, of suppressing them inside cells, of modifying their speciation so as to make them harmless or less toxic, of making them less soluble, of storing them in nontoxic form in the vacuole, etc.

Studies have shown that certain microorganisms are capable of concentrating metal ions by biosorption, such as Ag, Al, Au, Co, Cd, Cu, Cr, Fe, Hg, Mn, Ni, Pb, Pd, Pt, U, Th, Zn, etc., in dilute solutions (White et al., International Biodeterioration & Biodegradation, 35: 17-40, 1995; U.S. Pat. No. 6,355,172). Biosorption is the capacity of the biomass to bind heavy metals by means of nonselective physicochemical mechanisms via interactions with the functional groups of parietal compounds located at the surface of cells. For example, it has been proposed to use bacteria and mixtures of microorganisms to nonselectively biosorb heavy metals (U.S. Pat. No. 7,479,220; PCT application WO 03/011487).

Other methods use dead biomass or derived compounds originating from the culture of living organisms to depollute media contaminated with metals. The processes involved are biologically inactive, physicochemical mechanisms, such as ion exchange, for example with the polysaccharides present in cell walls, complexation or adsorption.

Biomass derived from algae (for example cell walls) has been used to purify metals contained in liquid effluents (U.S. Pat. No. 4,769,223; PCT application WO 86/07346; U.S. Pat. No. 5,648,313; PCT application WO 2006/081932).

There are few methods which call upon living organisms for the treatment of media polluted with radioactive compounds. Indeed, in the case of water contaminated with radioactive compounds or water located close to radioactive sources, it is necessary to use radiotolerant or radioresistant organisms, which are in addition capable of withstanding the chemical toxicity of the contaminants and of binding the compounds of interest in sufficient amount to be used in the context of an industrial process.

In the natural environment, organisms accumulating radioactive compounds are generally subjected to low radioactivity. For example, immediately after the accident at Chernobyl, for the aquatic media, the external dose rate of ionizing radiation of the reactor cooling tank water did not exceed 100 µGy/h and the maximum cumulative dose over one year was 0.01 Gy in 1986. The dose rate originating from the radionuclides deposited on the sediments in the Pripyat river, located in the 30 km zone around the power plant, increased, for its part, here and there, to 0.4 mGy/h immediately after the accident (Kryshev and Sazykina, Journal of Environmental Radioactivity, 28: 91-103, 1995).

In most cases, the resistance to ionizing radiation of the microorganisms proposed for depolluting materials or effluents contaminated with radioactivity and/or concentrating radioactive compounds has not been tested. This is because they are used to extract U (uranium) and Th (thorium) of which the activity of the main isotopes is low (for example, for $^{238}$U or $^{235}$U, the activity is 0.13 or 0.8 Bq/l for a solution containing 10 µg/l of $^{238}$U or $^{235}$U, respectively.

U.S. Pat. No. 4,320,093 proposes the use of fungi of the *Rhizopus* genus for extracting uranium or thorium contained in aqueous effluents. Patent GB 1472626 proposes the use of mutant single-cell green algae obtained by X-ray irradiation of single-cell green algae pre-accustomed to uranium, and patent GB 1507003 proposes the use of various microorganisms, in particular the fungus *Aspergillus niger*, and cyanobacteria of *Oscillatoria* type, for concentrating the uranium naturally present in sea water. U.S. Pat. No. 7,172,691 proposes the use of live photosynthetic algae of the *Chlorella, Scenedesmus, Oocystis* and *Chlamydomonas* genera for concentrating radioactive contaminants, and in particular uranium, from aqueous media containing a concentration of uranium of about 0-20 ppm, which represents an activity of 260 and 1600 Bq/l for $^{238}$U and $^{235}$U, respectively. In comparison, the activity of water from nuclear element storage pools which constitute the living environment of the microalga described hereinafter is approximately 300 000 Bq/l.

The most radioresistant organisms described to date are prokaryotes. The species *Deinococcus radiodurans* has an extraordinary capacity for resistance to ionizing radiation, grows under irradiations of 60 Gy/h and survives at doses of 15 kGy. However, this bacterium is naturally not very resistant to metals. For example, it does not tolerate cobalt (irrespective of the isotope), which inhibits its growth at 5 ppm, i.e. at approximately $10^{-4}$ mol/l (John et al., Symposium Chemical-biological Interactions In Contaminant Fate, Metal Toxicity In *Deinococcus radiodurans*, p. 426-428 in Preprints of Extended Abstracts Vol. 40 No. 2, 2000). Its use as a purifier of metals contained in radioactive media therefore requires genetic modifications in order to introduce genes which make it possible to accumulate the metals of interest. Thus, it has been proposed to genetically modify bacteria of the *Deinococcus* genus so as to express enzymes capable of detoxifying or of metabolizing organic compounds, metals or radionuclides, for the purposes of in situ bioremediation of nuclear waste sites (PCT application WO 01/23526). More recently, bacteria of the *Kineococcus radiotolerans* species have been isolated and purified from a radioactive waste site of high activity. These bacteria have been described as being capable of degrading organic contaminants in the presence of ionizing radiation, the dose rate of which is greater than 10 Gy/h, and their use for nonselective depollution of radionuclides by biosorption has been proposed (U.S. Pat. No. 7,160, 715).

Although they can be used for decontaminating media of which the radioactivity is very high, these two microorganisms have the drawback of being non-autotrophic, and therefore of requiring the external provision of carbonaceous nutrients in order to be able to be used in the form of live cultures. Furthermore, the culture thereof is more sensitive to contamination with other bacteria than that of autotrophic organisms, which, moreover, require a less rich culture medium.

A single form of radiotolerant autotrophic organism has been described (Farhi et al., 20: 104216, 2008). It is a microalga of the class Chlorophyceae, which tolerates ionizing radiation with an LD50 of 6 kGy, whereas, in general, the LD50s for resistance to ionizing radiation of algae are between 30 and 1200 Gy (IAEA, 1976, Effects of ionizing radiation on aquatic organisms and ecosystems. Technical reports series No. 172, International Atomic Energy Agency, Vienna).

The inventors have now isolated another radiotolerant microalga, belonging to the *Coccomyxa* genus (class Trebouxiophyceae: Pröschold and Leliaert, Unravelling the algae: the past, present, and future of algal systematics, CRC Press, Brodie and Lewis eds., 2007), and have discovered that, not only does this alga exhibit resistance to ionizing radiation that is even greater than that of the microalga described by Farhi et al. (2008, above), but that, in addition, it is capable of taking up and concentrating radioactive or nonradioactive metal ions in solution in an aqueous medium, and that it can grow in a radioactive medium.

This alga represents a new species of *Coccomyxa*, hereinafter referred to as *Coccomyxa actinabiotis*.

An axenic culture representative of this new species was deposited according to the treaty of Budapest on Jun. 23, 2009, with the Culture Collection of Algae and Protozoa (CCAP), Scottish Association for Marine Science, Dunstaffnage Marine Laboratory, GB-Oban, Argyll, PA37 1QA, UK, under number CCAP 216/25.

The algae of the *Coccomyxa actinabiotis* species are characterized in particular in that their genes corresponding to 18S ribosomal RNA-ITS1-5.85 ribosomal RNA-ITS2-26S ribosomal RNA (start) contain a sequence exhibiting at least 95%, and, in order of increasing preference, at least 96%, 97%, 98% or 99% identity with the sequence SEQ ID NO: 1.

The percentage identity indicated above is calculated after alignment of the sequences using the Clustal software (Larkin et al., Bioinformatics, 23, 2947-2948, 2007), on a comparison window consisting of the whole of the sequence SEQ ID NO: 1.

The algae of the *Coccomyxa actinabiotis* species can also be characterized in that the region corresponding to ITS1-5.8S rRNA-ITS2 exhibits at least 90% identity with the corresponding region of the sequence SEQ ID NO: 1. This threshold was estimated at 90% on the basis of the observations by the inventors, which show a maximum of 81% identity between this region in *Coccomyxa actinabiotis* and in other *Coccomyxae* and also a maximum of 88% identity between the ITS1-5.85 rRNA-ITS2 of the other *Coccomyxae* compared with one another (cf. table III hereinafter).

The sequence of the ribosomal RNA genes of *Coccomyxa actinabiotis* differs in particular from that of other species of the *Coccomyxa* genus through the presence, in the region corresponding to the 18S rRNA, of two inserts of approximately 500 bp (inserts represented in italics in FIG. 2). It also differs through the nature of its 18S rRNA gene (FIG. 3), and through that of its ITS1 and ITS2.

*Coccomyxa actinabiotis*, by virtue of its resistance to ionizing radiation, can grow in a radioactive medium, which allows it to take up and metabolize radioactive compounds other than metals (for example $^3H$ or $^{14}C$), in addition to being able to take up and concentrate radioactive or nonradioactive metal ions in solution in an aqueous medium.

Consequently, the subject of the present invention is the use of green algae of the *Coccomyxa* genus, and in particular of the *Coccomyxa actinabiotis* species defined above, for taking up at least one element chosen from the metals Ag, Co, Cr, Zn, Mn, Sb, Cs, Ni, Fe, actinides, or lanthanides, whether they are radioactive or not, or the radioisotopes $^{14}C$ and $^3H$, from an aqueous medium containing said metal or said radioisotope in solution.

More particularly, the subject of the present invention is a method for taking up at least one element chosen from the radioactive or nonradioactive metals Ag, Co, Cr, Zn, Mn, Sb, Cs, Ni, Fe, actinides or lathanides, or the radioisotopes $^{14}C$ and $^3H$ from an aqueous medium containing said element in solution, characterized in that said uptake is carried out by incubating green algae of the *Coccomyxa* genus in said aqueous medium.

Advantageously, said element is a metal chosen from Ag, Co, and the actinide U.

Also advantageously, said element is $^{14}C$. The amount of $^{14}C$ in the waste from nuclear plants in France has only been regulated individually for the last few years. However, $^{14}C$ is the principal radioactive pollutant emitted into the environment by nuclear plants, after tritium. For example, the basic nuclear plants of the Tricastin nuclear power station (4 sections of 900 MW) discharged 170 GBq of $^{14}C$ into the atmosphere and 15.9 GBq of $^{14}C$ in liquid effluents in 2009 (EDF Annual Report 2009). Reprocessing factories which use the Purex® process (for example, AREVA The Hague) discharge into the environment approximately 600 GBq/year of $^{14}C$ for reprocessing all of the fuel of a 1 GWe reactor (Toxicologie nucléaire environnementale et humaine [Environmental and human nuclear toxicology], eds Tec and Doc, Lavoisier, 2009).

According to one preferred embodiment of the present invention, said aqueous medium is a radioactive medium, i.e. a medium in which said algae are subjected to a dose rate that can range from a few µGy/h to 1 kGy/h. According to one preferred arrangement of this embodiment, the element to be taken up is a metal chosen from those indicated above, in the form of a radioactive isotope, or in the form of a mixture of isotopes.

The incubation time of the algae in the aqueous medium can vary in particular according to, firstly, the element(s) concerned and, secondly, the nature of the aqueous medium from which the uptake must be carried out. It will generally be at least 1 hour, and may range up to several months, or even several years. For example, if it is desired to take up only Ag, an incubation time of approximately 1 hour may be sufficient to take up the major part thereof, and of approximately 10 to 20 hours to take up virtually all thereof; if other metals are to be taken up, a longer incubation time, of at least 3 to 5 days, and advantageously of at least one week, may be used. As another example, if it is desired to take up $^{14}C$, an incubation time of 3 h, under the optimized conditions proposed in example 4 hereinafter, will be sufficient to take up the major part thereof.

The maximum incubation time that can be envisaged will in fact depend mainly on the capacity for growth and survival of the algae in the aqueous medium.

In the presence of light and carbon dioxide (introduced by contact with the ambient air, agitation of the cultures or bubbling), the algae of the *Coccomyxa* genus, and in particular of the *Coccomyxa actinabiotis* species, can grow and live for very long periods of time in weakly mineralized water (conductivity 1 to 1.5 µS/cm) at a pH of 5 to 6 and a temperature of 20 to 30° C., and in demineralized water (conductivity of 0.05 µS/cm), they can grow and live for 3 to 4 weeks. Since these green algae need light to carry out photosynthesis and produce their organic matter, their growth stops when they are placed in the dark.

Thus, according to one embodiment of the method in accordance with the present invention, the growth of the green algae of the *Coccomyxa actinabiotis* species can be controlled by controlling the illumination of the aqueous medium comprising said algae.

The *Coccomyxa actinabiotis* algae can also grow and live for several years in a weakly radioactive medium, where they are subjected to an irradiation of less than or equal to 0.15 mGy/h. They can withstand an irradiation of 1 Gy/h for up to approximately 1 month. They can also withstand an irradiation of 300 Gy/h for approximately a day and an irradiation of 100 Gy/h for approximately 3 days. In a very highly radioactive medium, they can withstand an irradiation of 1 kGy/h for up to 20 hours; if they are then transferred into a nonradioactive medium, they recover their growth capacity in less than two weeks. By way of indication, the limit of the range of low dose rates below which no biological effect has been detected can be placed at around 1 mSv/h (i.e. 1 mGy/h for γ-radiation). A low dose corresponds to a dose of less than 10 mSv/h. A dose rate greater than 1 mSv/h produces dangerous biological effects. For doses greater than 10-100 mSv, statistically observable effects appear. A high dose corresponds to an irradiation greater than 1 Gy, the value starting from which a deterministic effect begins to become apparent.

For implementing the process in accordance with the invention, the algae can be used in suspension in the aqueous medium from which the uptake is to be carried out, with shaking so as to avoid agglomeration thereof. They can also be attached to a solid support which is smooth, porous, or in the form of beads, placed in said aqueous medium.

The process can be transported, i.e. the algae are brought into contact with the medium to be depolluted in a chamber separate from the nuclear plant, or implemented in situ; in the latter case, the algae are then implanted directly in the medium to be depolluted.

In the case of an in situ uptake or decontamination process, the algae can reside in the plant as long as they do not impair operations. By way of indication, their growth can be controlled by the intensity of illumination (darkness or weak illumination), or the choice of the wavelength of the lamps (for example, yellow-green non-actinic light). Filtration of the water also makes it possible to control their growth by taking up the algae in suspension in the water. If it proves to be necessary to remove them, definite destruction of the algae may be accompanied by release of the metals, and will therefore have to be preferentially carried out by section in the plants, with recovery of the effluents containing a concentration of metals.

In the case of a transported process, at the end of the incubation, the algae having taken up the metals are harvested by conventional means (filtration, decanting, centrifugation, etc.). They can then be eliminated as waste, optionally after having been dried and/or burnt, without prior extraction of the metals that they contain.

Advantageously, the metals taken up by the algae can be recovered in order to recycle these metals.

This recovery can be carried out by any appropriate means. It is, for example, possible to non-destructively recover at least a part of the metals taken up by the algae, thereby making it possible, where appropriate, to reuse said algae, in particular for metals such as Ag and Cr, which, after uptake, remain largely at the level of the mucilage and of the cell surface. This recovery can be carried out by placing the algae in the presence of a complexing or acid solution. Thus, it can in particular be carried out for metals such as Ag, by treatment of the algae in an acidic medium, at a pH of from 1 to 2.5, preferably from 1.5 to 2, for 1 to 2 days.

For other metals, such as Cr, but also for the portion of metals such as Co which is bound at the level of the mucilage and of the cell surface, it can also be carried out by means of a treatment with a chelating agent, such as EDTA, at 0.1 mol/l for 1 h up to 3 days, preferably for approximately 1 day.

For metals such as Co which, after uptake by the algae, are sequestered inside the cells, the recovery can be carried out by treating the algae in an acidic medium, at a pH of 0.5, for 2 to 10 days, but without any guarantee of the subsequent viability of the cells.

The metals can also be recovered after destruction of the algae. This destruction can, for example, be carried out by lysis of the algae. It can also be carried out by incineration of the algae.

The process in accordance with the invention can be implemented in all cases where it is desired to extract radioactive or nonradioactive metals, and in particular those mentioned above, from an aqueous medium, for the purposes of mining operations, or of depollution of aqueous effluents containing metals, in particular of radioactive effluents.

In addition to their strong capacity for specifically taking up and concentrating the metals mentioned above (Ag, Co, Cr, Zn, Mn, Sb, Cs, Ni, Fe, actinides or lanthanides, whether they are radioactive or nonradioactive), the algae of the *Coccomyxa* genus, and in particular of the *Coccomyxa actinabiotis* species, also have properties of nonspecific uptake of other metals, in particular owing to their extracellular mucilage consisting of polysaccharides, which have the property of complexing cations.

The process in accordance with the invention is therefore particularly suitable for depolluting and for decontaminating aqueous media or soils (peat bogs, marshes) contaminated with radioactive or nonradioactive metals, and more particularly radioactive media, such as the water from storage pools or else the light water from secondary cooling circuits of nuclear power stations or reactors, or the effluents from nuclear power stations discharged into the environment.

The present invention can be implemented not only with single-cell green algae of the *Coccomyxa actinabiotis* species, but also with a mixture of microorganisms comprising single-cell green algae of the *Coccomyxa actinabiotis* species and at least one microorganism, in particular a bacterium, a fungus, a yeast, another single-cell alga and/or a multicellular plant, preferably radioresistant or radiotolerant, capable of concentrating metal ions in solution and/or of taking up and metabolizing radioactive compounds other than metals (for example, $^3$H or $^{14}$C). The multicellular plants and microorganisms that can be used in combination with the single-cell green algae of the *Coccomyxa actinabiotis* species are especially those mentioned above, in particular those which are radioresistant or radiotolerant. In the case where the present invention is applied to a radioactive aqueous medium, the incubation time of the mixture of microorganisms will depend on the individual resistance of the microorganisms making up the mixture. Similarly, the culture conditions may be adjusted in order to promote the growth of one or more microorganisms making up the mixture.

The present invention will be understood more clearly from the further description which follows, which refers to examples illustrating the isolation and the characterization of the *Coccomyxa actinabiotis* species, and also its use for decontaminating a radioactive aqueous medium. The examples are illustrated by means of the following figures:

FIGS. 1A and 1B represent photographs of microalgae according to the invention, observed by photon microscopy (Zeiss binocular Axioplan 2 microscope, magnification 1000 and 3000 for FIGS. 1A and 1B, respectively). FIG. 1B shows the joining of two flagellated cells.

FIG. 2 shows the sequence of the 18S rRNA-ITS1-5.85 rRNA-ITS2-26S rRNA ribosomal DNA genes (first 500 bases) of the *Coccomyxa actinabiotis* microalgae.

FIG. 3 shows the comparison of the sequences corresponding to the small subunit ribosomal RNA (18S rRNA) of the microalga CCAP 216/25, and of the other *Coccomyxa* species listed in the databases (after having taken away the 2 inserts specific for the sequences SEQ ID NO: 1), carried out by multisequence alignment by means of the Clustal W2 2.0.12 software.

Figure 5:
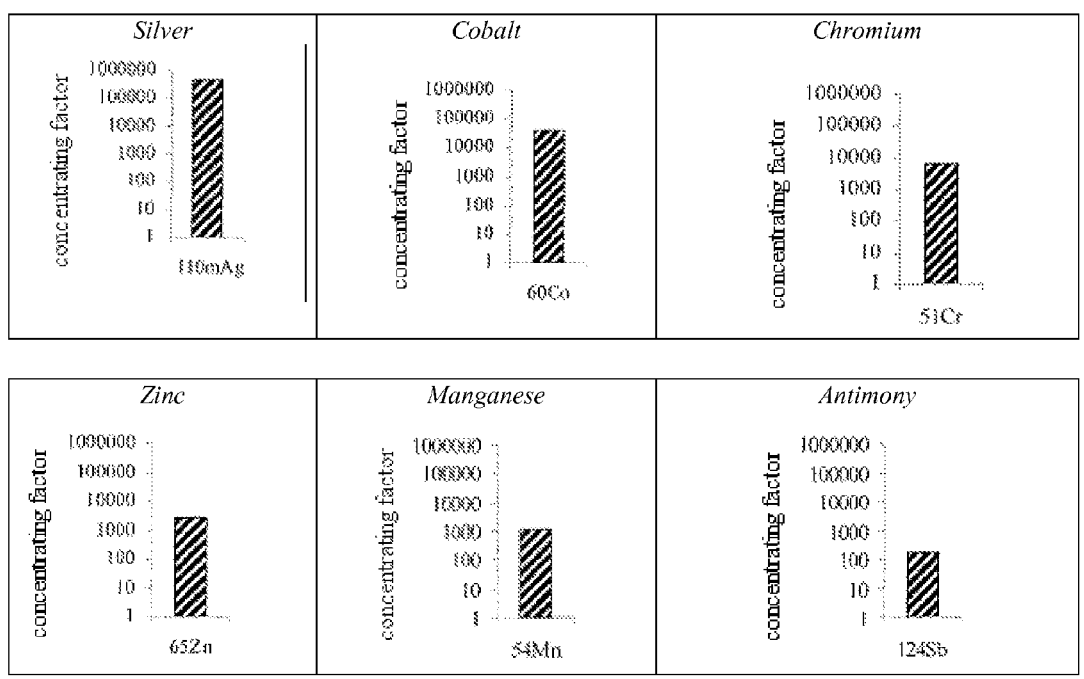

FIG. 5 illustrates the binding and concentrating of metals by *Coccomyxa* actinabiotis. The concentrating factors, defined as the ratio of the concentration of the metal adsorbed or absorbed in the microalgae (in atoms/g of fresh matter) to the concentration of the metal in the water (atoms/ml), obtained for the metals $^{110m}$Ag, $^{60}$Co, $^{51}$Cr, $^{65}$Zn, $^{54}$Mn and $^{124}$Sb, are represented.

FIGS. 6 to 8 show the kinetics for binding and for incorporation of metals, silver (FIGS. 6 and 7) and cobalt (FIG. 8), by the *Coccomyxa actinabiotis* microalgae, with (FIG. 7) or without (FIGS. 6 and 8) mucilage. The amounts of metal adsorbed-absorbed, as percentage, are represented as a function of exposure time (in hours). FIG. 6A: solution containing 110 µg/l of silver ions; FIG. 6B: solution containing 5.5 mg/l of silver ions; FIG. 7A: solution containing 1.1 mg/l of silver ions; FIG. 7B: solution containing 55 mg/l of silver ions; FIG. 8A: 19 µg/l of cobalt ions; FIG. 8B: 0.94 mg/l of cobalt ions; FIG. 8C: 4.8 mg/l of cobalt ions.

Figure 9:
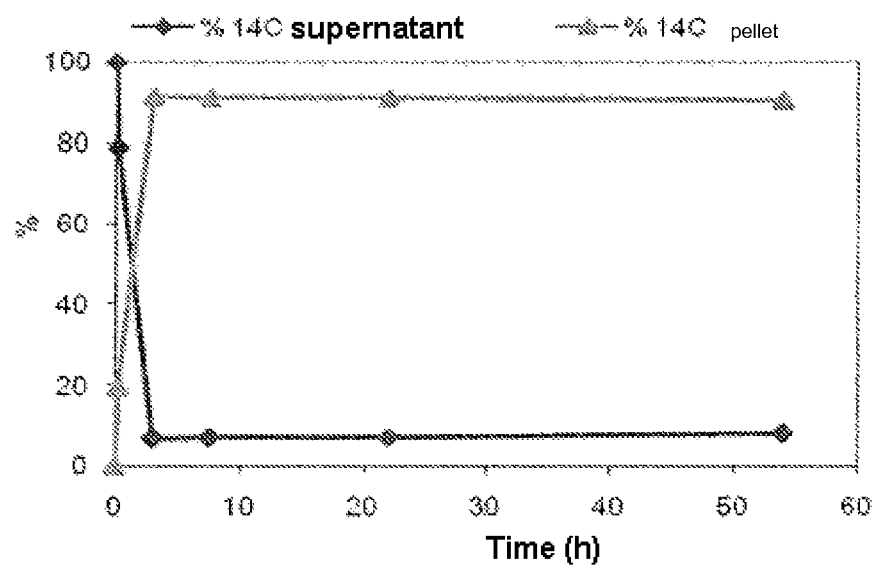

FIG. 9 shows the incorporation of $^{14}$C by a culture of *Coccomyxae actinabiotis*. The percentage of $^{14}$C in hydrogen carbonate form, in the pellet (triangles), which contains the algae, and in the culture supernatant (diamonds), is represented as a function of time, in hours.

Figure 10:
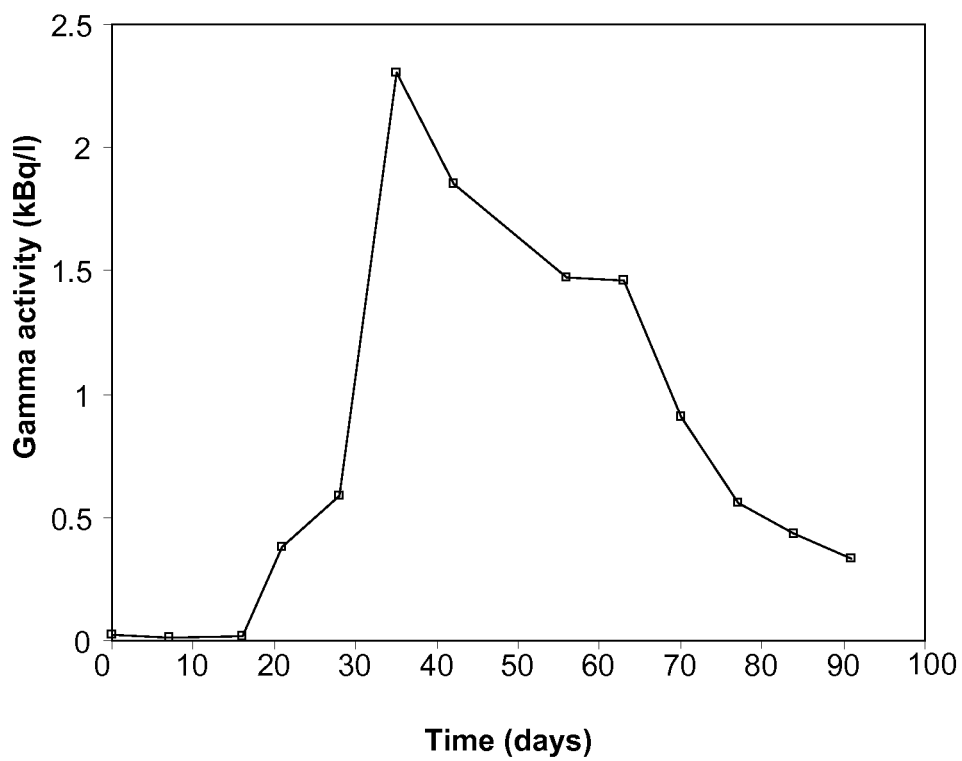

FIG. 10 represents the concentration of silver-110m, expressed in kBq/l, in a radioactive element storage pool, as a function of time (in days), in the presence of *Coccomyxae actinabiotis*.

EXAMPLE 1

Isolation and Characterization of *Coccomyxa actinabiotis*

The microalga was harvested from a spent fuel storage pool of a nuclear reactor. The water contained in this pool has a pH of 5.2 to 5.8 and a conductivity of from 1 to 1.5 µS/cm, is in contact with the ambient air and contains dissolved radioactive elements. Its temperature ranges between 23 and 30° C. and is on average 25° C. The radiological activity in the pool is very variable depending on the measuring points, low to very high. The gamma activity can reach several thousand Gy/h upon contact with spent fuel elements.

The presence of films of green organic matter was observed on the walls and various surfaces of this pool. Samples were taken and when observed under a microscope they showed that this was a single-cell green microalga.

Culture Conditions

The samples taken were stored and placed in culture in light, at a pH of from 5 to 6.5 and a temperature of 23° C., in sterile Erlenmeyer flasks closed with porous stoppers allowing gas exchange.

The following media were tested:

BBM culture medium (Bold's Basal Medium, Sigma), pure or diluted in demineralized water. BBM medium is conventionally used for culturing green algae;

BG11 culture medium (Rippka et al., "The Prokaryotes", vol. 1: 212-220, 1979; Sigma). This medium is conventionally used for culturing cyanobacteria;

weakly mineralized water (conductivity from 1 to 1.5 µS/cm), or demineralized water (conductivity of 0.05 µS/cm).

The composition of the BBM and BG11 culture media is indicated in table I hereinafter:

TABLE I

| | BBM | BG 11 |
|---|---|---|
| Constituents in g/L | | |
| NaNO$_3$ | 0.25 | 1.5 |
| KH$_2$PO$_4$ | 0.175 | |
| K$_2$HPO$_4$ | 0.075 | |
| K$_2$HPO$_4$•3H$_2$O | | 0.04 |
| MgSO$_4$•7H$_2$O | 0.075 | 0.075 |
| FeSO$_4$•7H$_2$O | 0.005 | |
| CaCl$_2$•2H$_2$O | 0.025 | 0.036 |
| NaCl | 0.025 | |
| Na$_2$EDTA | 0.01 | |
| KOH | 0.006 | |
| Citric acid | | 0.006 |
| Ferric ammonium citrate | | 0.006 |

TABLE I-continued

|  | BBM | BG 11 |
|---|---|---|
| Trace elements in mg/L | | |
| H$_3$BO$_4$ | 12.86 | 2.86 |
| MnCl$_2$•4H$_2$O | 1.81 | 1.81 |
| ZnSO$_4$•7H$_2$O | 0.222 | 0.222 |
| Na$_2$MoO$_4$•2H$_2$O | 0.39 | 0.39 |
| CuSO$_4$•5H$_2$O | 0.079 | 0.079 |
| Co(NO$_3$)$_2$•6H$_2$O | 0.049 | 0.049 |
| pH | 6.4 | 6.5 |

In the BG11 and BBM media, the microalgae grow with a similar exponential growth phase in the two media.

In the weakly mineralized water, or in the demineralized water with a conductivity of 0.05 µS/cm, the microalgae grow with a rapid growth phase in the short term, similar to that obtained with the BG11 and BBM media, but in the demineralized water with a conductivity of 0.05 µS/cm, their health deteriorates after 3 to 4 weeks, probably due to the depletion of reserves.

Algae were placed in culture on a solid agar BBM culture medium. Circular colonies were thus isolated, and then plated out individually on agar culture medium. This operation was repeated six times in order to obtain a pure culture originating from a single cell.

A sample of this culture (hereinafter referred to as microalga CCAP 216/25) was deposited according to the treaty of Budapest, on Jun. 25, 2009, with the Culture Collection of Algae and Protozoa (CCAP), Scottish Association for Marine Science, Dunstaffnage Marine Laboratory, GB-Oban, Argyll, PA37 1QA, UK, under number CCAP 216/25.

Morphological and Biochemical Characteristics

The microalgae isolated are single-cell microalgae. The cells, observed by photon microscopy and by confocal microscopy, are nucleated and oval in shape. Their average length is 6.8±0.9 µm and their average width is 3.8±0.6 µm. However, depending on their growth stage, it is possible to observe longer average lengths, up to 9-10 µm, or smaller ones, of about 5 µm, in particular just after division.

They contain a chloroplast (perhaps several) which contains chlorophyll and which is the site of photosynthesis. A protein granule, the pyrenoid, occupies part of the chloroplast. It is involved, inter alia, in the synthesis of starch. Other organelles, in particular the vacuole, occupy the rest of the cell.

In its vegetative form, the cell does not have mobility. Sometimes, certain individuals have two locomotor flagellae. They are either sexual cells or gametes, which perform reproduction, or zoospores which are involved in multiplication so as to allow dissemination of the species. The formation of these two types of cells is provided by the division of an initial cell or mother cell.

In culture on agar medium, the cells remain grouped in discoid aggregates.

Some differences distinguish the cells freshly sampled from the storage pool from those cultured for one month in BBM medium. The first have large storage granules, are mostly agglomerated to one another, held by a mucilage consisting of polysaccharides, and the mobility of their flagellated cells is reduced. When the algae cultured in the BBM medium are returned to radioactive and nutritive stress conditions, they go back to the morphology of those isolated from the storage pool water.

The second are more pigmented (bright green), generally well individualized, and their flagellated cells are very active when the culture is regularly stirred.

The cytological and behavioral modifications of this microalga in the hostile medium from which it was isolated can therefore be perceived as an adaptation to the particular physicochemical conditions (presence of ionizing radiation, presence of radioactive metals inducing oxidative and ionizing stress; lack of mineral salts, responsible for nutritive stress).

FIGS. 1A and 1B represent photographs of these microalgae observed by photon microscopy, one month after the introduction of a sample originating from the pool of the reactor in a BBM culture medium.

Starch, located in the chloroplast, can be revealed by staining with lugol (I$_2$+IK=iodinated water). A positive response to this reaction (brown to purplish blue coloration) makes it possible to categorize this microalga among the green algae (=chlorophyta).

The UV-visible absorption spectrum for this organism shows the presence of chlorophyll a (absorption peak at 663 nm), chlorophyll b (absorption peak at 647 nm) and carotene (absorption peak at 470 nm).

It is therefore a single-cell, eukaryote and freshwater taxon of green algae. It belongs to the kingdom Protista with affinity to plants, and therefore to the Protophyta. It lies in the division Chlorophyta or Green Algae since it contains chlorophylls a and b and carotene as photosynthetic pigments and its reserves are starch.

Amplification and Sequencing of the Ribosomal DNA Genes

The total DNA of microalga A isolated as described above was extracted by the method of Newman et al. (Genetics, 126: 875-888, 1990).

The region of the genome covering the 18S rRNA-ITS1-5.8S rRNA-ITS2-26S rRNA (first 500 bases) ribosomal DNA genes was amplified by PCR and sequenced.

The primers used are EAF3: TCGACAATCTGGTTG ATCCTGCCAG (SEQ ID NO: 2) and ITS055R: CTCCTTG-GTC CGTGTTTCAAGACGGG (SEQ ID NO: 3), conventionally used for amplifying microalga rRNA genes.

Figure 2:
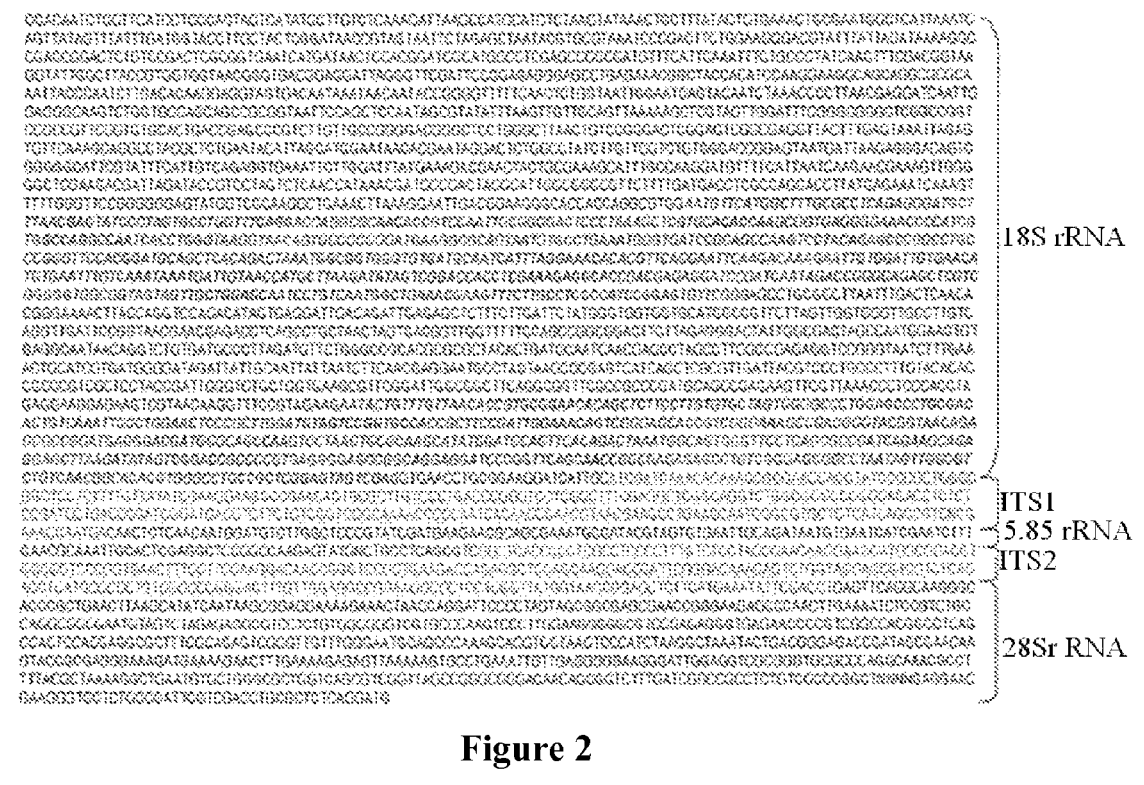

The amplification products obtained using the DNA isolated from two independent cultures are of 4 kb (i.e. 1 kb more than what is conventionally described for microalgae). The sequence of these amplification products is represented in FIG. 2, and also in the appended sequence listing under number SEQ ID NO: 1. This sequence contains 2 inserts of approximately 500 base pairs which are indicated in bold italics in FIG. 2 and which are specific to the microalga CCAP 216/25.

The BLASTN algorithm (Altschul et al. Nucleic Acids Research, 25: 3389-3402, 1997) was used to search, in the databases, for the sequences of ribosomal RNA genes exhibiting maximum identity with the sequence SEQ ID NO: 1. In order to carry out this search, the two sequences of approximately 500 base pairs which are indicated in bold italics in FIG. 2 were withdrawn. This search revealed that the species characterized closest to the microalga CCAP 216/25 belong to the *Coccomyxa* genus. The sequence SEQ ID NO: 1 contains, however, 2 specific inserts of approximately 500 base pairs, which are not found in the algae of the *Coccomyxa* genus that have been characterized up until now.

The comparison of the sequences corresponding to the ribosomal small subunit RNA (18S rRNA) of the CCAP 216/25 microalga, and of the other *Coccomyxa* species listed in the databases (performed after having withdrawn the two specific inserts of the sequence SEQ ID NO: 1) was carried out by multiple sequence alignment by means of the ClustalW2 2.0.12 software. The sequence alignment is presented in FIG. 3. Table II below gives the results of this sequence comparison. The sequences corresponding to the 18S rRNAs, which are compared in pairs, are indicated in the SEQ ID A and SEQ ID B columns, by reference to their number in the appended sequence listing.

TABLE II

| SEQ ID A | Name | Length (nt) | SEQ ID B | Name | Length (nt) | % identity |
|---|---|---|---|---|---|---|
| 4 | CCAP 216/25 | 2354 | 5 | Coccomyxa peltigerae | 1783 | 97 |
| 4 | CCAP 216/25 | 2354 | 6 | Coccomyxa chodatii | 1783 | 98 |
| 4 | CCAP 216/25 | 2354 | 7 | Coccomyxa sp flensburg | 1778 | 97 |
| 4 | CCAP 216/25 | 2354 | 8 | Coccomyxa glaronensis | 1797 | 96 |
| 4 | CCAP 216/25 | 2354 | 9 | Coccomyxa sp CPCC | 1797 | 96 |
| 4 | CCAP 216/25 | 2354 | 10 | Chlamydomonas_sp | 1558 | 92 |
| 5 | Coccomyxa peltigerae | 1783 | 6 | Coccomyxa chodatii | 1783 | 99 |
| 5 | Coccomyxa peltigerae | 1783 | 7 | Coccomyxa sp flensburg | 1778 | 96 |
| 5 | Coccomyxa peltigerae | 1783 | 8 | Coccomyxa glaronensis | 1797 | 96 |
| 5 | Coccomyxa peltigerae | 1783 | 9 | Coccomyxa sp CPCC | 1797 | 96 |
| 5 | Coccomyxa_peltigerae | 1783 | 10 | Chlamydomonas_sp | 1558 | 92 |
| 6 | Coccomyxa chodatii | 1783 | 7 | Coccomyxa sp flensburg | 1778 | 96 |
| 6 | Coccomyxa chodatii | 1783 | 8 | Coccomyxa glaronensis | 1797 | 96 |
| 6 | Coccomyxa chodatii | 1783 | 9 | Coccomyxa sp CPCC | 1797 | 97 |
| 6 | Coccomyxa_chodatii | 1783 | 10 | Chlamydomonas_sp | 1558 | 92 |
| 7 | Coccomyxa sp flensburg | 1778 | 8 | Coccomyxa glaronensis | 1797 | 99 |
| 7 | Coccomyxa sp flensburg | 1778 | 9 | Coccomyxa sp CPCC | 1797 | 99 |
| 7 | Coccomyxa_sp_flensburg | 1778 | 10 | Chlamydomonas_sp | 1558 | 91 |
| 8 | Coccomyxa glaronensis | 1797 | 9 | Coccomyxa sp CPCC | 1797 | 99 |
| 8 | Coccomyxa_glaronensis | 1797 | 10 | Chlamydomonas_sp | 1558 | 91 |
| 9 | Coccomyxa sp CPCC | 1797 | 10 | Chlamydomonas sp | 1558 | 91 |

This sequence comparison shows that the species closest to the CCAP 216/25 strain are *Coccomyxa chodatii* strain SAG 216-2 (SEQ ID NO: 6), *Coccomyxa peltigerae* strain SAG 216-5 (SEQ ID NO: 5), *Coccomyxa* sp. Flensburg fjord 2 (EU127471), *Coccomyxa glaronensis* strain CCALA 306 (AM167525) and *Coccomyxa* sp. strain CPCC 508 (AM981206) with, respectively, 98%, 97%, 97%, 96% and 96% sequence identity. These strong identity scores obtained for the CCAP 216/25 strain compared with the *Coccomyxa* genus are close to those obtained after comparison of the sequences of the *Coccomyxae* with one another and far from the score obtained for the sequence comparison with a single-cell microalga belonging to another genus (*Chlamydomonas* sp. CCMP681) (EF106784) (cf. FIG. 3). This indicates that the CCAP 216/25 strain belongs to the *Coccomyxa* genus.

Moreover, the comparison of the sequences of the ITS region of the CCAP 216/25 strain with those of the other *Coccomyxae* was also carried out. Table III below gives the results of this sequence comparison. The sequences of the ITS1-5.8S rRNA-ITS2 regions which are compared in pairs are indicated in columns I and II. The sequences of the *Coccomyxa actinabiotis* (CCAP 216/25), *Coccomyxa chodatii* SAG 216-2 and *Coccomyxa peltigerae* SAG 216-5 strains are indicated by reference to their number in the appended sequence listing, namely, respectively, SEQ ID NOS 11, 12 and 13. For the following strains, of which the sequences of the ITS1-5.8S rRNA-ITS2 regions are accessible in the GenBank database, the corresponding accession numbers are also indicated in table III:

AY293964: *Coccomyxa peltigerae* var. *variolosae*

AY293965: *Coccomyxa solarinae* var. *croceae*

AY293966: *Coccomyxa solarinae* var. *bisporae*

AY293967: *Coccomyxa solarinae* var. *saccatae*

AY293968: *Coccomyxa chodatii*

AY328522: *Coccomyxa peltigerae* strain SAG 216-5

AY328523: *Coccomyxa subellipsoidea* strain SAG 216-13

AY328524: *Coccomyxa rayssiae* strain SAG 216-8

U66945: *Chlamydomonas callosa*

U66956: *Dunaliella tertiolecta*

AF376740: *Pandorina morum*

TABLE III

| I | Length (nt) | II | Length (nt) | % identity |
|---|---|---|---|---|
| SEQ ID 11 | 761 | SEQ ID 12 | 617 | 81 |
| SEQ ID 11 | 761 | SEQ ID 13 | 708 | 79 |
| SEQ ID 11 | 761 | AY293964 | 610 | 78 |
| SEQ ID 11 | 761 | AY293965 | 650 | 73 |
| SEQ ID 11 | 761 | AY293966 | 651 | 73 |
| SEQ ID 11 | 761 | AY293967 | 651 | 73 |
| SEQ ID 11 | 761 | AY293968 | 619 | 76 |
| SEQ ID 11 | 761 | AY328522 | 725 | 73 |
| SEQ ID 11 | 761 | AY328523 | 702 | 75 |
| SEQ ID 11 | 761 | AY328524 | 696 | 76 |
| SEQ ID 11 | 761 | U66945 | 625 | 43 |
| SEQ ID 11 | 761 | U66956 | 598 | 45 |
| SEQ ID 11 | 761 | AF376740 | 626 | 27 |
| SEQ ID 12 | 617 | SEQ ID 12 | 708 | 87 |
| SEQ ID 12 | 617 | AY293964 | 610 | 83 |
| SEQ ID 12 | 617 | AY293965 | 650 | 82 |
| SEQ ID 12 | 617 | AY293966 | 651 | 83 |
| SEQ ID 12 | 617 | AY293967 | 651 | 83 |
| SEQ ID 12 | 617 | AY293968 | 619 | 92 |
| SEQ ID 12 | 617 | AY328522 | 725 | 84 |
| SEQ ID 12 | 617 | AY328523 | 702 | 80 |
| SEQ ID 12 | 617 | AY328524 | 696 | 94 |
| SEQ ID 12 | 617 | U66945 | 625 | 38 |
| SEQ ID 12 | 617 | U66956 | 598 | 31 |
| SEQ ID 12 | 617 | AF376740 | 626 | 26 |
| SEQ ID 13 | 708 | AY293964 | 610 | 97 |
| SEQ ID 13 | 708 | AY293965 | 650 | 99 |
| SEQ ID 13 | 708 | AY293966 | 651 | 99 |
| SEQ ID 13 | 708 | AY293967 | 651 | 99 |
| SEQ ID 13 | 708 | AY293968 | 619 | 88 |
| SEQ ID 13 | 708 | AY328522 | 725 | 94 |
| SEQ ID 13 | 708 | AY328523 | 702 | 80 |
| SEQ ID 13 | 708 | AY328524 | 696 | 86 |
| SEQ ID 13 | 708 | U66945 | 625 | 37 |
| SEQ ID 13 | 708 | U66956 | 598 | 51 |
| SEQ ID 13 | 708 | AF376740 | 626 | 34 |
| AY293964 | 610 | AY293965 | 650 | 97 |
| AY293964 | 610 | AY293966 | 651 | 97 |
| AY293964 | 610 | AY293967 | 651 | 97 |
| AY293964 | 610 | AY293968 | 619 | 83 |
| AY293964 | 610 | AY328522 | 725 | 96 |
| AY293964 | 610 | AY328523 | 702 | 78 |
| AY293964 | 610 | AY328524 | 696 | 85 |
| AY293964 | 610 | U66945 | 625 | 41 |
| AY293964 | 610 | U66956 | 598 | 50 |
| AY293964 | 610 | AF376740 | 626 | 48 |
| AY293965 | 650 | AY293966 | 651 | 99 |
| AY293965 | 650 | AY293967 | 651 | 99 |
| AY293965 | 650 | AY293968 | 619 | 88 |

TABLE III-continued

| I | Length (nt) | II | Length (nt) | % identity |
|---|---|---|---|---|
| AY293965 | 650 | AY328522 | 725 | 98 |
| AY293965 | 650 | AY328523 | 702 | 80 |
| AY293965 | 650 | AY328524 | 696 | 85 |
| AY293965 | 650 | U66945 | 625 | 37 |
| AY293965 | 650 | U66956 | 598 | 45 |
| AY293965 | 650 | AF376740 | 626 | 34 |
| AY293966 | 651 | AY293967 | 651 | 99 |
| AY293966 | 651 | AY293968 | 619 | 88 |
| AY293966 | 651 | AY328522 | 725 | 98 |
| AY293966 | 651 | AY328523 | 702 | 79 |
| AY293966 | 651 | AY328524 | 696 | 85 |
| AY293966 | 651 | U66945 | 625 | 37 |
| AY293966 | 651 | U66956 | 598 | 51 |
| AY293966 | 651 | AF376740 | 626 | 34 |
| AY293967 | 651 | AY293968 | 619 | 88 |
| AY293967 | 651 | AY328522 | 725 | 98 |
| AY293967 | 651 | AY328523 | 702 | 79 |
| AY293967 | 651 | AY328524 | 696 | 85 |
| AY293967 | 651 | U66945 | 625 | 37 |
| AY293967 | 651 | U66956 | 598 | 51 |
| AY293967 | 651 | AF376740 | 626 | 34 |
| AY293968 | 619 | AY328522 | 725 | 87 |
| AY293968 | 619 | AY328523 | 702 | 82 |
| AY293968 | 619 | AY328524 | 696 | 96 |
| AY293968 | 619 | U66945 | 625 | 37 |
| AY293968 | 619 | U66956 | 598 | 40 |
| AY293968 | 619 | AF376740 | 626 | 37 |
| AY328522 | 725 | AY328523 | 702 | 83 |
| AY328522 | 725 | AY328524 | 696 | 88 |
| AY328522 | 725 | U66945 | 625 | 37 |
| AY328522 | 725 | U66956 | 598 | 51 |
| AY328522 | 725 | AF376740 | 626 | 34 |
| AY328523 | 702 | AY328524 | 696 | 84 |
| AY328523 | 702 | U66945 | 625 | 38 |
| AY328523 | 702 | U66956 | 598 | 36 |
| AY328523 | 702 | AF376740 | 626 | 35 |
| AY328524 | 696 | U66945 | 625 | 37 |
| AY328524 | 696 | U66956 | 598 | 31 |
| AY328524 | 696 | AF376740 | 626 | 26 |
| U66945 | 625 | U66956 | 598 | 58 |
| U66945 | 625 | AF376740 | 626 | 59 |
| U66956 | 598 | AF376740 | 626 | 51 |

This sequence comparison shows a 73% to 81% identity of the sequence of the CCAP 216/25 strain compared with the other *Coccomyxae* strains referenced, of the same order as the scores obtained for the comparison of the ITS region of the referenced *Coccomyxae* with one another (78% to 99%), and very far from that obtained for the comparison with other genera (about from 30 to 50%).

Furthermore, it is found that the sequence corresponding to the 18S rRNA of the CCAP 216/25 strain is different than that of all the *Coccomyxae* referenced up until now, in particular in that it has two insertions of approximately 500 base pairs.

The latter two points indicate that it is a *Coccomyxa* species different than all those referenced to date.

These results therefore indicate that the microalga isolated belongs to the *Coccomyxa* genus, but that its DNA differs sufficiently from that of the other species of *Coccomyxae* listed in the databanks, in particular by virtue of its two insertions in the 18S rRNA DNA and ITS1 and ITS2 for it to be considered that this is a new species, which will be named herein *Coccomyxa actinabiotis*.

Resistance to Abiotic Stresses

*Coccomyxa actinabiotis* is resistant to desiccation, to cold and to the dark for 48 h.

It is also resistant to pure heavy water for 48 h (respiration and photosynthesis of algae exposed for 24 h and 48 h to 50%, 80% and 100% $D_2O$, in the dark, and their recovery after 24 h in a normal medium and also respiration and photosynthesis of algae exposed to 24 h to light in 50% $D_2O$ shows that the heavy water has, under these conditions, no effect on these physiological parameters).

This resistance to heavy water makes it possible to propose the use of *Coccomyxa actinabiotis* (and more generally of algae of the *Coccomyxa* genus) for the synthesis of deuterated compounds.

*Coccomyxa actinabiotis* is also resistant to acetone, to alcohol, to acids and to ultrasound.

The resistance to ionizing radiation of the algae was tested by exposing them to various doses of gamma radiation derived from spent fuel elements of which the irradiation is decreasing. The mortality after irradiation was determined by vital staining (neutral red).

*Coccomyxa actinabiotis* is resistant in the long term (more than about ten years) to moderate irradiation (150 µGy/h).

It withstands exposure for several days to a dose rate of 300 Gy/h and for a few hours to a dose rate of 3000 Gy/h.

It also withstands exposure for 20 h to a flow rate of 1 kGy/h.

Figure 4:
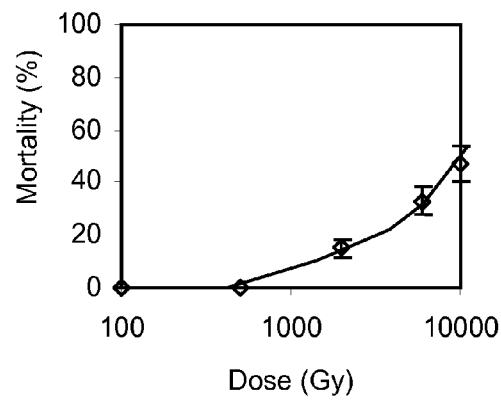
FIG. 4 shows the percentage mortality of *Coccomyxa actinabiotis* as a function of the dose of irradiation in gray (Gy).

FIG. 4 shows the percentage mortality of *Coccomyxa actinabiotis* as a function of the dose of irradiation. The dose of ionizing radiation which causes the death of half the population is more than 10 kGy (45% mortality at 10 kGy).

*Coccomyxa actinabiotis* also remarkably withstands exposure to 20 kGy (80%±5% mortality, i.e. 20%±5% survivors). In the case of this strong irradiation at 20 kGy, it recolonizes the medium in a few weeks. In four weeks, the culture has recovered a third of its initial photosynthetic activity before irradiation, and it recovers in two weeks a population density equal to that of nonirradiated or weakly irradiated samples.

EXAMPLE 2

Concentrating of Radioactive Metals by *Coccomyxa actinabiotis*

Binding and Concentrating of Metals

The microalgae freshly sampled from the storage pool (approximately 10 milligrams of fresh mass) were placed in the presence, under illumination (200 lux), for 1 year, of regularly renewed demineralized water, at pH 5.5, with a conductivity of 1.2 µS/cm, containing for example 400 Bq/l of $^{60}$Co, 1100 Bq/l of $^{110m}$Ag, 1700 Bq/l of $^{124}$Sb, 5000 Bq/l of $^{51}$Cr, 400 Bq/l of $^{65}$Zn, 300 Bq/l of $^{54}$Mn. The water is radioactive essentially owing to the presence of tritium (approximately 300 000 Bq/l) and of $^{14}$C (approximately 20 000 Bq/l). This composition is similar to that of the water from spent fuel storage pools. The algae multiplied slowly during this contact time.

The concentrations of the radionuclides were measured at equilibrium in the waters and in the algae by γ-spectrometry.

The concentration factors for each metal ($^{110m}$Ag, $^{60}$Co, $^{51}$Cr, $^{65}$Zn, $^{54}$Mn and $^{124}$Sb), defined as the ratio of the concentration of the metal adsorbed or absorbed in the microalgae (in atoms/g of fresh matter) to the concentration of the metal in the water (atoms/ml), were thus obtained.

The results are illustrated by FIG. 5.

These results show that the microalgae very strongly concentrate silver and cobalt (concentration factor=450 000 and 40 000, respectively), and also chromium to a lesser extent (concentration factor=6000). The least concentrated elements also have a significant concentration factor (concentration factor=6000, 3000, 1200 and 200 for chromium, zinc, manganese and antimony, respectively).

Another experiment was carried out by placing 250 mg of fresh mass of microalgae originating from cultures in BBM medium in the presence of 100 mm of demineralized water which has a composition similar to that of the water from the spent fuel storage pools, namely pH 5.5, conductivity 1.2

µS/cm, containing 280 Bq/l of $^{60}$Co, 530 Bq/l of $^{58}$Co, 66 Bq/l of $^{110m}$Ag, 1460 Bq/l of $^{124}$Sb, 1180 Bq/l of $^{51}$Cr, 120 Bq/l of $^{65}$Zn, Bq/l of $^{54}$Mn and also tritium (260 000 Bq/l) and $^{14}$C (10 000 Bq/l). After one day of culture, the percentage of each isotope fixed is 100%, 100%, 94%, 94%, 90%, 48% and 30% for $^{110m}$Ag, $^{65}$Zn, $^{60}$Co, $^{58}$Co, $^{54}$Mn, $^{51}$Cr and $^{124}$Sb, respectively.

Extraction of the Metals from the Microalgae

Experiments in which the metals bound by the algae are solubilized were carried out by incubating these algae (70 mg of fresh matter) in 5 ml of demineralized water, or of demineralized water supplemented with HCl at various concentrations. In neutral medium, the metals are not extracted.

The cations most retained are $^{60}$Co, $^{108m}$Ag and $^{110m}$Ag. They remain bound to the cell for low concentrations of HCl (pH 4.5 to 2.5). They begin to be released exponentially below a threshold pH of 2.5, Co being the most solidly bound since it is at most 35% extracted after 6 days of exposure at pH 0.5, whereas Ag is 90% extracted under the same conditions. At pH 1.5, 10% of Ag and 2% of Co are extracted after 6 days of exposure. For $^{51}$Cr, there is no threshold pH, it is extracted from pH=4.5 linearly up to a maximum of 25% at pH=0.5 after 6 days of exposure.

Other experiments were carried out in the presence of a 0.1 M solution of EDTA with a pH of 4.5. Under these conditions, 35% of the $^{51}$Cr contained in the algae, but only 1% of the $^{60}$Co and less than 0.5% of $^{108m}$Ag and $^{116m}$Ag, are extracted after 2 days of exposure.

These experiments show that Cr remains predominantly at the surface, whereas Co is probably predominantly sequestered inside the cells and Ag is distributed between the surface and the inside of the cells.

EXAMPLE 3

Kinetics for Binding of Metals, Resistance to their Toxicity and Amounts Bound

Kinetics of Binding and Incorporation of Ag and Co

The kinetics of binding of metals by the *Coccomyxa actinabiotis* microalgae, and also the amounts adsorbed-absorbed, were determined in the case of a monovalent cation, Ag$^+$, and of a divalent cation, Co$^{2+}$.

Silver

Two series of experiments were carried out: one with algae having a coating of mucilage, the thickness of which, evaluated by optical microscopy, is about 1 µm or more ("algae with mucilage"), the other with algae cultured in BBM medium and having little or no mucilage ("algae without mucilage").

20 mg of algae (compacted fresh mass) and 90 ml of solution of Ag$^+$ at various concentrations are introduced into Erlenmeyer flasks. The 20 mg of algae are prepared as follows: sample taken from a round-bottomed culture flask, centrifugation for 20 minutes at 3000 rpm, washing twice in demineralized water (suspension, centrifugation). The culture medium is thus removed and there is no risk of it complexing the silver.

The algae without mucilage are brought into contact with solutions containing 0.11 mg/L and 5.5 mg/L of Ag$^+$.

The algae with mucilage are brought into contact with solutions containing 22 µg/L, 1.1 mg/L and 55 mg/L of Ag$^+$.

The Erlenmeyer flasks are placed on illuminated shakers and samples of 5 ml are taken for various exposure times in order to monitor the binding kinetics for each of the initial concentrations of silver. The samples are centrifuged for 10 minutes at 4500 rpm in order to separate the algae which have concentrated the metal. The metal content is then analyzed in the pellet (algae) and in the supernatant.

The results are illustrated in FIG. 6 for the algae without mucilage, and in FIG. 7 for the algae with mucilage.

For the algae with or without mucilage, very rapid silver absorption kinetics are observed in the first hours, followed by a plateau.

At the plateau, the algae without mucilage bind all the silver if its initial concentration is 0.11 mg/l and bind 75% thereof if its initial concentration is 5.5 mg/l.

The algae with mucilage bind all the silver if its initial concentration is 1.1 mg/l and bind 20% thereof if its initial concentration is 55 mg/l.

The rapid accumulation of silver by the algae can be explained by two phenomena. Firstly, by chelation outside the microalgae by the abundant mucilage, consisting of polymers of sugars and derivatives, which has the property of chelating cations. Secondly, by active and/or passive incorporation of the silver inside the algae via channels or transporters. The numerous transmembrane ion channels for example perform nonselective passive transport of Na$^+$ ions, K$^+$ ions or possible monovalent metals such as Ag$^+$, to the cytoplasm, all the more readily if the concentration gradient is high.

Thus, the concentrating of silver by *Coccomyxa* corresponds to adsorption on the mucilage and the parietal compounds, added to which is intracellular absorption via transmembrane ion channels and active transporters.

Cobalt

Experiments were carried out with algae having little or no mucilage, according to the same protocol as that described above for silver. The algae were exposed to initial cobalt concentrations of 19 µg/L, 0.94 mg/L and 4.8 mg/L.

The results are represented in FIG. 8(A-C).

Initial rapid adsorption, possibly coupled with absorption, is observed. It is, however, less marked for cobalt than for silver. The absorption then continues gradually over several days. The concentration of intracellular cobalt does not reach a maximum, but continues to increase more than a week after the beginning of the exposure.

The cobalt absorption mechanism therefore appears to be different than that of silver. The divalent Co$^{2+}$ ions cannot in fact use the same ion channels as the Ag$^+$ ions because of their larger ionic radius. It is likely that cotransporters, responsible for the absorption of divalent metals essential for cell growth (Fe$^{2+}$, Mg$^{2+}$, etc.) or active transporters, such as ATP-dependent ABC pumps known as transmembrane transporters of cadmium Cd$^{2+}$, or Zn$^{2+}$ ATPases, carry out the absorption of cobalt. This active transport would explain a moderate but long-lasting absorption.

Maximum Metal Concentrations Tolerated

The limiting doses supported by *Coccomyxa actinabiotis* were investigated by exposure of the algae to silver or to cobalt for one week (20 mg of microalgae (fresh mass) in 100 ml of deionized water containing Ag or Co ions at various concentrations).

The algae without mucilage are less resistant to silver metal toxicity than the algae with mucilage. The mucilage could prevent a rapid and strong afflux of metal into the cytoplasm at the beginning of exposure. By forming an ion-binding barrier, it limits diffusion to the transmembrane channels and rapid and massive importing of toxic metals. These metals would then be moderately and gradually absorbed and could be stored in forms not aggressive for the cell. *Coccomyxae actinabiotis* without mucilage do not survive at silver concentrations greater than 250 µg/L, whereas *Coccomyxae actinabiotis* with mucilage withstand extracellular silver concentrations of at least 50 mg/L.

The cobalt intolerance threshold is greater than $Co^{2+}$ concentrations of 50 mg/l and 800 mg/l for *Coccomyxa actinabiotis* without mucilage and with mucilage, respectively. No notable effect was observed on the microalgae cultured for one week under these conditions.

Maximum Metal Concentrations Bound

The algae can bind much higher amounts of Ag and of Co than what might be expected by passive binding, in particular owing to their synthesis of abundant mucilage and to active mechanisms of incorporation and detoxification.

Generally, metals are toxic for organisms.

Silver is generally toxic for organisms at $10^{-7}$-$10^{-5}$ mol/l (Ratte H T, Environ. Toxicol. Chem. 18: 89-108, 1999).

Radioresistant organisms such as *Deinococcus radiodurans* do not grow in the presence of cobalt at $10^{-4}$ mol/l (John et al., 2000, above). However, the *Coccomyxa actinabiotis* microalga does grow in the presence of $10^{-4}$ mol/l of cobalt.

*Coccomyxa actinabiotis* algae brought into contact, in a BBM culture medium diluted 10 times, with an equivalent of $6.7 \times 10^{-4}$ mol of silver per gram of alga bind up to 43.7 mg of silver per gram of fresh mass, i.e. approximately 450 mg/g of dry mass.

This amount of silver bound is much higher than those reported in the literature. The literature reports silver concentrations in terrestrial plants of between 0.01 and 150 µg of silver/g of dry mass, i.e. approximately 0.001 to 15 µg of silver/g of fresh mass, and silver concentrations in algae of between 3 µg/g and 7 mg/g of dry mass, i.e. approximately 0.3 µg to 0.7 mg of silver/g of fresh mass. The amount of silver bound by *Coccomyxa actinabiotis* is even greater than the amount of silver that can be accumulated by bacteria which exhibit extremely high tolerance to silver: silver-hyperaccumulating bacteria accumulate up to 300 mg of silver/g of dry mass (Ratte, 1999, above; Charley et al., Arch. Microbiol. 123: 239-244, 1979). Furthermore, the most highly silver-accumulating organisms are not radioresistant.

*Coccomyxa actinabiotis* algae brought into contact for 45 days with an equivalent of $3.8 \times 10^{-4}$ mol of cobalt per gram of alga in a BBM nutritive medium diluted 10 times bind 12.1 mg of metal per gram of fresh biomass. In 6 days, algae brought into contact with an equivalent of $1.0 \times 10^{-3}$ mol of cobalt per gram of alga in a BBM nutritive medium diluted 10 times bind 1.53 mg of metal per gram of fresh biomass. These values are much higher than those reported in the literature. The average concentration of cobalt in plants varies between 0.1 and 115 µg/g of dry mass, i.e. approximately 0.01 to 11 µg/g of fresh mass, and cobalt-hyperaccumulating plants bind up to 4.3 mg thereof/g of dry mass (Bresson et al., Toxicologie nucléaire, environnementale et humaine [Nuclear, environmental and human toxicology], publisher Lavoisier 2009, editions TEC and DOC. Chap. 29 Cobalt, p. 553-573), i.e. approximately 0.4 mg/g of fresh mass. The most highly cobalt-accumulating organisms cited in the literature are not radioresistant.

EXAMPLE 4

Fixing of Carbon 14

Carbon 14 constitutes, with tritium, the principal radioactive pollutant discharged into the environment by nuclear plants (8 to 25 GBq of $^{14}C$/year in the liquid waste from EDF plants). $^{14}C$ waste has been regulated only since 2008. For the moment, there is no specific $^{14}C$ treatment. The regulations in terms of $^{14}C$ in liquid radioactive waste vary from one plant to another. The threshold is set at 150-400 GBq for an EDF power station (ordered 2008). $^{14}C$ is discharged into liquid effluents essentially in the form of $^{14}CO_2$, carbonate ($^{14}CO_3^{2-}$ or $H^{14}CO_3^-$) $^{14}CO$ and a small percentage in unidentified organic form. Like all plants, the *Coccomyxa* green microalga is capable of incorporating carbon in the form of $^{12}CO_2$ via photosynthesis. The isotopic discrimination of $^{14}C$ with respect to $^{12}C$ is negligible in biological processes. However, contrary to what might be deduced therefrom, the fixing of $^{14}C$ by the *Coccomyxa actinabiotis* microalga is not at all obvious. For example, the alga does not fix $^{14}C$ at pH 8, but fixes it at pH 7.

Furthermore, the fixing of $^{14}C$ via biological processes such as photosynthesis can be carried out only with live photosynthetic biomass.

The impact of $^{14}C$ on the physiology of the microalgae and the parameters which make it possible to carry out and optimize its accumulation by these microorganisms were determined.

$^{14}C$ is assayed in the algae and in the water by liquid scintillation. The microalgae are brought into contact with $^{14}C$ in the form of carbonate $CO_3^{2-}$ in acid-base equilibrium with $HCO_3^-$ and $CO_2$ (pKa of 6.4 and 10.3) and also in the form of acetate.

Impact of $^{14}C$ on the Physiology of the Microalgae

The impact of the presence of $^{14}C$ on the physiology of the algae was evaluated by monitoring the growth of the cells. The presence of $^{14}C$ alone, up to 20 000 Bq/l, has no impact on growth, compared with that of a culture not exposed to $^{14}C$.

Cells placed in culture in water from a spent nuclear fuel storage pool, containing gamma emitters and enriched with 300 000 Bq/l of $^{14}C$, also experienced growth of their population for 8 days.

Parameters Influencing the Incorporation of $^{14}C$ by the Algae
Chemical Form of $^{14}C$ The algae incorporate the carbon dioxide inorganic form in equilibrium with the hydrogen carbonate, just as they do the acetate organic form. The $CO_2$ is incorporated into the cells via photosynthesis (6 $CO_2$+12 $H_2O$+hv→$C_6H_{12}O_6$+6 $O_2$+$H_2O$). The acetate is used by the metabolism in the form of acetyl coenzyme A and in particular in the main energy cycle of the cell (Krebs cycle).

pH

The influence of the pH on the incorporation of $^{14}C$ in hydrogen carbonate form was studied in the range 6.9 to 8.5. The optimum pH is 6.9 and allows the incorporation of from 80 to 90% of the $^{14}C$ present in the medium when the containers in which the bringing into contact is carried out are hermetically closed. At this pH, 25% of the $^{14}C$ is in the form of dissolved $CO_2$. It is necessary to close the containers in order to avoid rapid degassing of the $^{14}CO_2$ in equilibrium with $H^{14}CO_3^-$.

The amount of $^{14}C$ incorporated by the algae is low at pH 7.5 (a few %) and zero at pH 8.5.

Initial Conditions for Culturing the Microalgae

The physiological state of the cells at the moment they are brought into contact with the $^{14}C$ has an influence on the rate of incorporation of the $^{14}C$. The microalgae incorporate the $^{14}C$ much more rapidly when they have been cultured beforehand in a medium richer in nutrients (BBM medium diluted two-fold preferable to a BBM medium diluted ten-fold). Thus, the optimum time for bringing the algae into contact with a medium containing 20 000 Bq/l of $^{14}C$ is 50 h if the culture is derived from a BBM medium diluted ten-fold, whereas it is reduced to 3 h if the culture is derived from a BBM medium diluted two-fold.

Density of the Algae

The amount of $^{14}C$ incorporated in a given period of time increases with the density of the algae in the range $5 \times 10^6$ to $15\times10^6$ cells/ml. By way of example, 50 h are necessary for an algal population with an initial cell density of $5\times10^6$ cells/ml to incorporate 70% of the amount of $^{14}C$ present in the medium (20 000 Bq/l), whereas 7.5 h are sufficient for an algal population with an initial cell density of $15\times10^6$ cells/ml to incorporate 90% thereof.

Illumination Intensity

The $^{14}C$ incorporation experiments were carried out under weak illumination (50 to 70 μmol of photons/m²/s). However, the photosynthetic activity increases with the illumination, to reach a maximum starting from 500 μmol of photons/m²/s. The measurement of the maximum photosynthetic activity of the algae, carried out with an illumination of more than 500 μmol of photons/m²/s, shows that the algae are capable of consuming much more $^{12}CO_2$ under stronger illumination (at least 30 times more than at the light intensities at which the $^{14}C$ incorporation experiments were carried out).

$^{14}C$ Concentration

Regardless of the initial concentration of $^{14}C$ in the range 2000 to 20 000 Bq/l (which corresponds to the concentrations present in the water from the pools of certain nuclear plants), at pH 6.9, the algae rapidly and strongly incorporate the $^{14}C$. The maximum rate of $^{14}C$ incorporation by a population of algae derived from a culture in BBM medium diluted two-fold is 20 Bq/h/$10^6$ cells for a $^{14}C$ concentration of 6000 Bq/l and is 60 Bq/h/$10^6$ cells for a $^{14}C$ concentration of 20 000 Bq/l. The amounts incorporated are about 80-90%.

The incorporation of $^{14}C$ in hydrogen carbonate form, at pH 6.9, by a culture of *Coccomyxae actinabiotis* derived from a BBM medium diluted two-fold, at the initial concentration of $5\times10^6$ cells/ml, illuminated with 70 μmol of photons/m²/s, was measured. The $^{14}C$ concentration is 6000 Bq/l. After centrifugation of samples at the various times, the $^{14}C$ content is analyzed in the pellet (algae) and in the supernatant. The results are illustrated by FIG. 9.

Optimum Operating Conditions for $^{14}C$ Purification
  pH 6.9
  cells initially cultured in a medium rich in nutrients (BBM diluted two-fold)
  cell density of $15\times10^6$ cells/ml
  intense illumination (500 μmol of photons/m²/s)
  contact time: a few hours Performance Levels
  90% decontamination

*Coccomyxae actinabiotis* can therefore be used to decontaminate the carbon 14 contained in water resulting from nuclear plants: 90% decontamination in 3 to 7 hours, under optimized conditions.

EXAMPLE 5

Binding of Uranium

The algae according to the invention can also be used to take up uranium and transuranium elements.

*Coccomyxae actinabiotis* microalgae harvested from a round-bottomed culture flask and washed three times with Milli-Q water in order to remove the culture medium were brought into contact, with shaking and at a concentration equivalent to 60 mg of algae by fresh mass/100 ml of solution, with a solution of uranyl nitrate having a concentration of $10^{-8}$ mol/l. In 26 h, the algae bind 45% of the amount of uranium initially present in solution. Under these conditions, the factor of uranium bioconcentration by the *Coccomyxae actinabiotis* algae is 1300 l/kg of fresh mass, i.e. approximately 13 000 l/kg of dry mass. The bioconcentration factors reported in the literature are about 120-140 l/kg for freshwater or seawater algae (Paquet et al., Toxicologie nucléaire, environnementale et humaine [Nuclear, environmental and human toxicology], publisher Lavoisier 2009, editions TEC and DOC. Chap. 23 Uranium, p. 411-443).

EXAMPLE 6

Decontamination of Storage Pool Water by Means of *Coccomyxae actinabiotis* Via In Situ Action The *Coccomyxae actinabiotis* microalgae were placed on horizontal supports in a fuel element cooling pool of a nuclear plant. This pool is filled with water having an average pH of 5.5, an average conductivity of 1.2 μS/cm, and an average temperature of 25° C., and contains radioactive metal elements owing to the parts which are stored therein. The pool is in contact with the ambient air and is illuminated by neon light. The light intensity at the surface of the water is 200 lux. Depending on the parts stored in the pool, the dose rate at the level of the algae ranges from about 100 μGy/h to a few tens of Gy/h. Under these conditions, *Coccomyxae actinabiotis* is capable of colonizing the supports on which it is placed, and can live thereon and reproduce thereon for years. The dose rate can sporadically reach a few hundred Gy/h.

The total activity and also the nature and the activity of each γ-emitter present were determined by performing counting by γ-spectrometry on samples of 50 ml of water and of 100 mg of algae sampled from the supports. The results obtained after a residence time of 5 years are given in table IV below.

TABLE IV

| Radionuclide | Activity (Bq) of 1 ml of water | Activity (Bq) of 1 g of microalgae |
| --- | --- | --- |
| $^{51}Cr$ | 1.73 | 10543 |
| $^{54}Mn$ | 0.15 | 168 |
| $^{60}Co$ | 0.64 | 24733 |
| $^{65}Zn$ | 0.13 | 363 |
| $^{108m}Ag$ | <limit of detection = 0.02 | 556 |
| $^{110m}Ag$ | 0.006 | 2671 |
| $^{124}Sb$ | 0.87 | 149 |

These results show that the algae are approximately 10 000 times more active than the water in which they live: the radioelements are actually concentrated on the outside and on the inside of the microalgae.

The silver in particular has virtually disappeared from the water. The cobalt and the chromium were very strongly concentrated.

EXAMPLE 7

Decontamination of Storage Pool Water by Means of *Coccomyxae actinabiotis* Via In Situ Action and Comparison with Conventional Methods An experiment in which water from a radioactive element storage pool, with a total volume of 361 m³, was decontaminated was carried out in situ using the *Coccomyxa actinabiotis* microalga in suspension in the pool to be depolluted. At t=14 days, two safety rods from a reactor were introduced into the pool. These rods release silver 110m. The water is usually purified by ion exchange resins which bind the radionuclides. At t=30 d, the purification by the resins was stopped. From t=35 d to t=56 d, the water was purified by uptake of the radionuclides by the algae in suspension in the pool. These algae, and also the radiological activity collected, bind to micropore filters (50 mm diameter, 60 mm height) installed in a mobile pool robot at the surface. The filters, which are highly active, are changed every 2 days.

FIG. 10 shows the concentration of silver 110m in this pool as a function of time, expressed in number of days. The decrease in the $^{110m}$Ag concentration observed between 35 and 56 d is due to its uptake by the algae present in the pool and which bind to the filters.

Starting from t=60 d, the ion exchange resins were put back into operation. FIG. 10 shows purification of the radioelements with similar efficiency whether it is carried out with the microalgae or with the ion exchange resins. In total, during this experiment, 740 MBq of γ emitters (of which 470 for $^{110m}$Ag, 180 for $^{124}$Sb and 90 for $^{60}$Co) were removed from the pool by the algae in 21 days.

EXAMPLE 8

Decontamination of Nuclear Plant Water by Means of *Coccomyxae actinabiotis* Via a Transported Method Water originating from a spent nuclear element storage pool was brought into contact with *Coccomyxae actinabiotis* (50 ml of water in contact with 9×10$^8$ cells, i.e. 140 mg of algae by fresh mass, originating from culture and rinsed beforehand three times with Milli-Q water). The water initially contains the radionuclides listed in table V below.

The assaying of the water and of the algae 24 h after the bringing into contact shows an elimination of 92% of the γ-activity of the water in 24 h.

Table V below indicates the initial composition of the water, according to the total γ-activity measured and the γ-activity measured per radionuclide, and the percentage of γ-emitting radionuclides bound by the algae at 24 h.

TABLE V

|  | Total | $^{54}$Mn | $^{60}$Co | $^{110m}$Ag | $^{137}$Cs | $^{238}$U |
|---|---|---|---|---|---|---|
| Initial γ-activity in the water (Bq/l) | 161.9 | 9.2 | 42.4 | 22.7 | 66.5 | 21 |
| % binding | 92 | 100 | 72 | 100 | 100 | 95 |

The binding is therefore 100% for silver 110m, manganese 54 and cesium 137, 72% for cobalt 60, and 95% for uranium 238.

EXAMPLE 9

Control of the Proliferation of the Microalgae

The microalgae are photosynthetic. They need light to perform photosynthesis and produce their organic matter. In the highly nutrient-depleted medium which corresponds to the various media and effluents from nuclear power stations, their growth can therefore be controlled by illumination. In order for them to grow at a given place, it is sufficient to illuminate them. In the pool where they were uncovered, they proliferate preferably close to the light sources. When they are placed in the dark for a period of 2 days to 1 month, their growth stops. Their growth can also be controlled by illuminating them with a light which allows little or no photosynthesis, for example with a yellow-green-colored non-actinic lamp.

Filtration of the water makes it possible to take up the algae in suspension in the water, and to control the growth thereof.

The invention claimed is:

1. An isolated single-cell green alga of the *Coccomyxa* genus, characterized in that it belongs to the *Coccomyxa actinabiotis* species defined by the presence, in the 18S ribosomal RNA-ITS1-5.8S rRNA ITS2-26S rRNA genes, of a sequence exhibiting at least 95% identity with the sequence SEQ ID NO: 1.

2. The isolated single-cell green alga as claimed in claim 1, which is the *Coccomyxa actinabiotis* strain deposited on Jun. 25, 2009 with the Culture Collection of Algae and Protozoa (CCAP) under number CCAP 216/25.

3. A method for taking up at least one element chosen from the metals Ag, Co, Cr, Zn, Mn, Sb, Ni, Fe, Cs, actinides and lanthanides, and the radioisotopes $^{14}C$ and $^{3}H$, from an aqueous medium containing said metal or said radioisotope in solution, characterized in that said uptake is carried out by incubating the isolated single-cell green algae of the *Coccomyxa* genus of claim 1 in said aqueous medium.

4. A method for taking up at least one element chosen from the metals Ag, Co, Cr, Zn, Mn, Sb, Ni, Fe, Cs, actinides and lanthanides, and the radioisotopes $^{14}C$ and $^{3}H$, from an aqueous medium containing said metal or said radioisotope in solution, characterized in that said uptake is carried out by incubating the isolated single-cell green algae of the *Coccomyxa* genus of claim 2 in said aqueous medium.

5. The method as claimed in claim 3, characterized in that said aqueous medium is a radioactive medium.

6. The method as claimed in claim 5, for taking up a metal chosen from Ag, Co, Cr, Zn, Mn, Sb, Ni, Fe, Cs, actinides and lanthanides, characterized in that said metal is in the form of a radioactive isotope, or in the form of a mixture of isotopes.

7. The method as claimed in claim 3, characterized in that the isolated single-cell green algae of the *Coccomyxa* genus is a *Coccomyxa actinabiotis* species and the growth of the isolated single-cell green algae of the *Coccomyxa actinabiotis* species is controlled by controlling the illumination of said aqueous medium.

8. The method as claimed in claim 7, characterized in that the element taken up is a metal, and in that it comprises a step of recovering said metal from the algae.

9. A method for decontaminating a radioactive aqueous medium containing at least one element chosen from the metals Ag, Co, Cr, Zn, Mn, Sb, Ni, Fe, Cs, actinides and lanthanides, and the radioisotopes $^{14}$C and $^{3}$H, comprising incubating the isolated single-cell green algae of claim 1 in the radioactive aqueous medium.

10. A method for decontaminating a radioactive aqueous medium containing at least one element chosen from the metals Ag, Co, Cr, Zn, Mn, Sb, Ni, Fe, Cs, actinides and lanthanides, and the radioisotopes $^{14}$C and $^{3}$H, comprising incubating the isolated single-cell green algae of claim 2 in the radioactive aqueous medium.

\* \* \* \* \*

UNITED STATES PATENT AND TRADEMARK OFFICE
CERTIFICATE OF CORRECTION

| | | |
|---|---|---|
| PATENT NO. | : 8,673,620 B2 | Page 1 of 1 |
| APPLICATION NO. | : 13/578410 | |
| DATED | : March 18, 2014 | |
| INVENTOR(S) | : Corinne Rivasseau et al. | |

It is certified that error appears in the above-identified patent and that said Letters Patent is hereby corrected as shown below:

On the Title Page, (73) Assignees should read: Commissariat a L'Energie Atomique et Aux Energies Alternatives, Paris (FR); Institut Max Von Laue-Paul Langevin, Grenoble Cedex 9, (FR); Centre National de la Recherche Scientifique, Paris (FR); Museum National D'Histoire Naturelle, Paris (FR)

Signed and Sealed this
Ninth Day of September, 2014

Michelle K. Lee
*Deputy Director of the United States Patent and Trademark Office*